US007504556B2

(12) United States Patent
Madison et al.

(10) Patent No.: US 7,504,556 B2
(45) Date of Patent: Mar. 17, 2009

(54) TRANSGENIC SYSTEMS FOR THE MANUFACTURE OF POLY(2-HYDROXY-BUTYRATE-CO-3-HYDROXYHEXANOATE)

(75) Inventors: Lara Madison, Bridgewater, MA (US); Gjalt W. Huisman, San Carlos, CA (US); Oliver P. Peoples, Arlington, MA (US)

(73) Assignee: Metabolix, Inc., Cambridge, MA (US)

( * ) Notice: Subject to any disclaimer, the term of this patent is extended or adjusted under 35 U.S.C. 154(b) by 638 days.

(21) Appl. No.: 10/703,906

(22) Filed: Nov. 7, 2003

(65) Prior Publication Data

US 2004/0172675 A1 Sep. 2, 2004

Related U.S. Application Data

(63) Continuation of application No. 09/235,875, filed on Jan. 22, 1999, now Pat. No. 7,455,999.
(60) Provisional application No. 60/072,198, filed on Jan. 22, 1998.

(51) Int. Cl.
  *C12N 15/82* (2006.01)
  *C12N 15/87* (2006.01)
  *A01H 1/00* (2006.01)

(52) U.S. Cl. .................. 800/281; 800/288; 800/298; 800/306; 800/312; 800/317.2; 800/317.3; 800/320; 800/322

(58) Field of Classification Search ................. 536/23.1, 536/23.2; 435/419, 465; 800/278, 281, 284, 800/287, 288, 298
See application file for complete search history.

(56) References Cited

U.S. PATENT DOCUMENTS

| 4,826,493 | A |   | 5/1989 | Martini et al. |
| 4,876,331 | A |   | 10/1989 | Doi |
| 4,900,299 | A |   | 2/1990 | Webb |
| 4,910,145 | A |   | 3/1990 | Holmes et al. |
| 4,968,611 | A |   | 11/1990 | Traussing et al. |
| 5,213,976 | A |   | 5/1993 | Blauhut et al. |
| 5,225,227 | A |   | 7/1993 | Yalpani |
| 5,229,158 | A |   | 7/1993 | Yalpani |
| 5,238,833 | A |   | 8/1993 | Sanders et al. |
| 5,245,023 | A |   | 9/1993 | Peoples et al. |
| 5,266,422 | A |   | 11/1993 | Reusch et al. |
| 5,286,842 | A |   | 2/1994 | Kimura |
| 5,292,860 | A |   | 3/1994 | Shiotani et al. |
| 5,461,139 | A |   | 10/1995 | Gonda et al. |
| 5,470,727 | A |   | 11/1995 | Mascarenhas et al. |
| 5,480,794 | A |   | 1/1996 | Peoples et al. |
| 5,512,482 | A |   | 4/1996 | Voelker et al. |
| 5,512,669 | A |   | 4/1996 | Peoples et al. |
| 5,516,883 | A |   | 5/1996 | Hori et al. |
| 5,534,432 | A |   | 7/1996 | Peoples et al. |
| 5,563,239 | A |   | 10/1996 | Hubbs et al. |
| 5,849,894 | A |   | 12/1998 | Clemente et al. |
| 6,091,002 | A | * | 7/2000 | Asrar et al. ............. 800/288 |
| 6,316,262 | B1 |  | 11/2001 | Huisman et al. |
| 6,586,658 | B1 |  | 7/2003 | Peoples et al. |

FOREIGN PATENT DOCUMENTS

| BR | 9302312-0 | 2/1995 |
| CA | 2006508 | 8/1990 |
| DE | 195 33 459 | 11/1996 |
| JP | 7-79788 | 3/1995 |
| JP | 7-135985 | 5/1995 |
| WO | WO 91/13207 | 9/1991 |
| WO | WO 92/09210 | 6/1992 |
| WO | WO 92/09211 | 6/1992 |
| WO | WO 93/23554 | 11/1993 |
| WO | WO 95/15260 | 6/1995 |
| WO | WO 95/20614 | 8/1995 |
| WO | WO 95/20615 | 8/1995 |
| WO | WO 95/20621 | 8/1995 |
| WO | WO 96/00263 | 1/1996 |
| WO | WO 96/17369 | 6/1996 |
| WO | WO 97/08931 | 3/1997 |
| WO | WO 98/00557 | 1/1998 |
| WO | WO 00/11188 | 3/2000 |

OTHER PUBLICATIONS

Nawrath C. et al. PNAS vol. 91; pp. 12760-12764.*
Schubert P. et al., (J. of Bacteriology 1988; vol. 170, No. 12, p. 5837-5847).*
Boynton Z., et al. (J. of Bacteriology Jun. 1996, vol. 178, No. 11, p. 3015-3024.*
Hoffman N. et al. (FEMS Microbiology Letters, 2000, p. 253-259).*
van der Leij, F. et al. (Canadian Journal of Microbiology, 1995; vol. 41, Supplement 1; pp. 222-238).*
Boynton Z. et al. (J. of Bacteriology Jun. 1996, vol. 178, No. 11, p. 3015-3024).*
Fukui et al. (J. of Bacteriol. vol. 179: pp. 4821-4830, 1997).*
Abe, et al., "Biosynthesis from gluconate of a random copolyester consisting of 3-hydroxybutyrate and medium-chain-length 3-hydroxyalkanoates by *Pseudomonas* sp. 61-3," Int. J. Biol. Macromol. 16:115-19 (1994).
Agostini, et al., "Synthesis and Characterization of Poly-β-Hydroxybutyrate. I. Synthesis of Crystalline DL Poly-β-Hydroxybutyrate from DL-β-Butyrolactone," Polym. Sci. 9:2775-87 (1971).

(Continued)

*Primary Examiner*—Russell Kallis
(74) *Attorney, Agent, or Firm*—Pabst Patent Group LLP

(57) ABSTRACT

Methods for engineering transgenic organisms that synthesize polyhydroxyalkanoates (PHAs) containing 3-hydroxyhexanoate as comonomer have been developed. These processes are based on genetically engineered bacteria such as *Escherichia coli* or in plant crops as production systems which include PHA biosynthetic genes from PHA producers. In a preferred embodiment of the method, additional genes are introduced in wild type or transgenic polyhydroxybutyrate (PHB) producers, thereby creating new strains that synthesize 3HH monomers which are incorporated into PHAs. The 3HH monomer preferably is derived in microbial systems using butanol or butyrate as feedstocks, which are precursors of 3-hydroxyhexanoyl-CoA. Pathways for in vivo production of butyrol-CoA specifically encompassing butyryl-CoA dehydrogenase activity are provided.

22 Claims, 10 Drawing Sheets

OTHER PUBLICATIONS

Amos & McInerney, "Composition of poly-β-hydroxyalkanoate from Syntrophomonas wolfei grown on unsaturated fatty acid substrates," Arch. Microbiol. 155:103-06 (1991).

Bouquin, et al., "Resistance to trifluoroperazine, a calmodulin inhibitor, maps to the fabD locus in *Escherichia coli*," Mol Gen Genet. 246(5):628-37 (1995).

Boynton, et al., "Cloning, sequencing, and expression of clustered genes encoding beta-hydroxybutyryl-coenzyme A (CoA) dehydrogenase, crotonase, and butyryl-CoA dehydrogenase from *Clostridium acetobutylicum* ATCC 824," J Bacteriol. 178(11):3015-24 (1996).

Brandl, et al., "Ability of the phototrophic bacterium *Rhodospirillum rubrum* to produce various poly (beta-hydroxyalkanoates): potential sources for biodegradable polyesters," Int. J. Biol. Macromol. 11:49-55 (1989).

Byrom, "Miscellaneous Biomaterials" in Biomaterials (D. Byrom, ed.) pp. 333-359 (MacMillan Publishers, London 1991).

Caballero, et al., "Biosynthesis and characterization of hydroxybutyrate-hydroxycaproate copolymers," Int J Biol Macromol. 17(2):86-92 (1995).

Clark & Rod, "Regulatory mutations that allow the growth of *Escherichia coli* on butanol as carbon source," J Mol Evol. 25(2):151-8 (1987).

De Luca, "Molecular characterization of secondary metabolic pathways," Ag. Biotech News Info 5:225N-229N (1997).

De Smet, et al., "Characterization of intracellular inclusions formed by *Pseudomonas oleovorans* during growth on octane," J. Bacteriol. 154:870-78 (1983).

Dennis, et al., "Formation of poly(3-hydroxybutyrate-co-3-hydroxyhexanoate) by PHA synthase from *Ralstonia eutropha*," J Biotech 64:177-86 (1998).

Doi, et al., "Microbial synthesis and characterization of poly(3-hydroxybutyrate-co-3-hydroxyhexanoate)," Macromolecules 28: 4822-4828 (1995).

Dong & Stams, "Localization of the enzymes involved in H2 and formate metabolism in *Syntrophospora bryantii*," Antonie Van Leeuwenhoek. 67(4):345-50 (1995).

Dubois, et al., "Macromolecular Engineering of Polylactones and Polylactides. 12. Study of the Depolymerization Reactions of Poly (∊-caprolactone) with Functional Aluminum Alkoxide End Groups," Macromolecules 26:4407-12 (1993).

Engel & Massay, "The purification and properties of butyryl-coenzyme A dehydrogenase from *Peptostreptococcus elsdenii*," Biochem J. 125(3):879-87 (1971).

Fukui & Doi, "Cloning and analysis of the poly(3-hydroxybutyrate-co-3-hydroxyhexanoate) biosynthesis genes of *Aeromonas caviae*," J Bacteriol. 179(15):4821-30 (1997).

Fukui, et al., "Enzymatic synthesis of poly-beta-hydroxybutyrate in *Zoogloea ramigera*," Arch Microbiol. 110(23):149-56 (1976).

George & Smibert, "Fumarate reduction and product formation by the Reiter strain of *Treponema phagedenis*," J Bacteriol. 152(3):1049-59 (1982).

Gross, et al., "Polumerization of βMonosubstituted-βpropiolactones Using Trialkylaluminum-Water Catalytic Systems and Polymer Characterization," Macromolecules 21:2657-68 (1988).

Hall, et al., "Cloning of the Nocardia corallina polyhydroxyalkanoate synthase gene and production of poly-(3-hydroxybutyrate-co-3-hydroxyhexanoate) and poly-(3-hydroxyvalerate-co-3-hydroxyheptanoate)," Can J Microbiol. 44(7):687-91 (1998).

Hartel & Buckel, "Sodium ion-dependent hydrogen production in *Acidaminococcus fermentans*," Arch Microbiol. 166(5):350-6 (1996).

Haywood, et al., "Characterization of two 3-ketothiolases possessing differing substrate specificities in the polyhydroxyalkanoate synthesizing organism *Alcaligenes eutrophus*," FEMS Microbiol. Lett. 52:91-96 (1988).

Haywood, et al., "The importance of PHB-synthase substrate specificity in polyhydroxyalkanoate synthesis by *Alcaligenes eutrophus*," FEMS Microbiol. Lett. 57:1-6 (1989).

Hocking & Marchessault, "Biopolyesters" in Chemistry and Technology of Biodegradable Polymers, (Griffin, Ed.) pp. 48-96, Chapman and Hall:London, 1994.

Hocking & Marchessault, "Syndiotactic poly[(R,S)-β-hydroxybutyrate] isolated from methylaluminum-catalyzed polymerization," Polym. Bull. 30:163-70 (1993).

Holmes, "Biologically Produced (R)-3-hydroxyalkanoate Polymers and Copolymers," in Developments in Crystalline Polymers (D.C. Bassett, Ed.), pp. 1-65, Elsevier:London, 1988.

Hori, et al., "Ring-Opening Copolymerization of Optically Active β-Butyrolactone with Several Lactones Catalyzed by Distannoxane Complexes: Synthesis of New Biodegradable Polyesters," Macromolecules 26:4388-90 (1993).

Hori, et al., "Ring-Opening Polymerization of optically Active β-Butyrolactone Using Distannoxane Catalysts: Synthesis of High Molecular Weight Poly(3-hydroxybutyrate)," Macromolecules 26:5533-34 (1993).

Huisman, et al., "Synthesis of poly(3-hydroxyalkanoates) by mutant and recombinant *Pseudomonas strains*," Appl. Microbiol Biotech 38:1-5 (1992).

Huisman, et al., "Synthesis of poly-3-hydroxyalkanoates is a common feature of fluorescent pseudomonads," Appl Environ Microbiol. 55(8):1949-54 (1989).

Imamura, et al., "Purification of the multienzyme complex for fatty acid oxidation from *Pseudomonas fragi* and reconstitution of the fatty acid oxidation system," J Biochem (Tokyo). 107(2):184-9 (1990).

Jesudason & Marchessault, "Synthetic Poly[(R,S)-β-hydroxyalkanoates] with Butyl and Hexyl Side Chains," Macromolecules 27:2595-602 (1994).

Kato, et al., "Production of a novel copolyester of 3-hydroxybutyric acid with a medium-chain-length 3-hydroxyalkanoic acids by *Pseudomonas* sp. 61-3 from sugars," Appl. Microbiol. Biotechnol. 45:363-70 (1996).

Kemnitzer, et al., "Preparation of predominantly Syndiotactic Poly(β-hydroxybutyrate) by the Tributylin Methoxide Catalyzed Ring-Opening Polymerization of racemic β-Butyrolactone," Macromolecules 26:1221-29 (1993).

Lafferty, et al., "Microbial Production of Poly-b-hydroxybutyric acid" in Biotechnology (Rehm & Reed, Eds.), pp. 135-176, Verlagsgesellschaft:Weinheim, 1988.

Le Borgne & Spassky, "Stereoelective polymerization of β-butyrolactone," Polymer 30:2312-19 (1989).

Lee, et al., "Biosynthesis of copolyesters consisting of 3-hydroxybutyric acid and medium chain length 3-ydroxyalkanoic acids from 1,3-butanediol or from 3-hydroxybutyrate by *Psuedomonas* sp. A33," Appl. Microbiol. Biotechnol. 42:901-09 (1995).

Madan, et al., "Purification and properties of NADP-dependent L(+)-3-hydroxybutyryl-CoA dehydrogenase from *Clostridium kluyveri*," Eur J Biochem. 32(1):51-6 (1973).

Martinez, et. al., "pACYC184-derived cloning vectors containing the multiple cloning site and lacZ reporter gene of pUC8/9 and pUC18/19 plasmids," Gene 68: 159-62 (1988).

Miller & Jenesel "Enzymology of butyrate formation by *Butyrivibrio fibrisolvens*," J Bacteriol. 138(1):99-104 (1979).

Mitomo et al., "Fractional and structural change of microbial poly(3-hydroxybutyrate-4-hydroxybutyrate," Reports on Progress in Polymer Physics in Japan 37: 671-672 (1994).

Mullany, et al., "Genes encoding homologues of three consecutive enzymes in the butyrate/butanol-producing pathway of *Clostridium acetobutylicum* are clustered on the *Clostridium difficile* chromosome," FEMS Microbiol Lett. 124(1):61-7 (1994).

Müller & Seebach, "Poly(hydroxyalkanoates): A Fifth Class of Physiologically Important Organic Biopolymers," Angew. Chem. Int. Ed. Engl. 32: 477-502 (1993).

Pieper & Steinbuchel, "Identification, cloning and sequence analysis of the poly(3-hydroxyalkanoic acid) synthase gene of the gram-positive bacterium *Rhodococcus ruber*," FEMS Microbiol Lett. 75(1):73-9 (1992).

Ploux, et al., "The NADPH-linked acetoacetyl-CoA reductase from *Zoogloea ramigera*. Characterization and mechanistic studies of the cloned enzyme over-produced in *Escherichia coli*," Eur J Biochem. 174(1):177-82 (1988).

Pramanik, et al., "Five different enzymatic activities are associated with the multienzyme complex of fatty acid oxidation from *Escherichia coli*," J Bacteriol. 137(1):469-73 (1979).

Prieto, et al., "Engineering of stable recombinant bacteria for production of chiral medium-chain-length poly-3-hydroxyalkanoates," Applied and Environmental Microbiology 65(8):3265-3270 (1999).

Sambrook, et al., in Molecular Cloning, a laboratory manual, (2nd Ed.), Cold Spring Harbor Laboratory Press:Cold Spring Harbor, NY, 1992.

Shimamura, et al., "Physical properties and biodegradability of microbial poly(3-hydroxybutyrate-co-3-hydroxyhexanoate," Macromolecules 27: 878-880 (1994).

Steinbüchel & Valentin, "Diversity of bacterial polyhydroxyalkanoic acids," FEMS Microbiol. Lett. 128:219-28 (1995).

Steinbüchel & Wiese, "A *Pseudomonas strain* accumulating polyesters of 3-hydroxybutyric acid and medium-chain-length 3-hydroxyalkanoic acids," Appl. Microbiol. Biotechnol. 37:691-97 (1992).

Steinbüchel, "Polyhydroxyalkanoic Acids" in Biomaterials (Byrom Ed.), pp. 123-213, MacMillan Publishers:London, 1991.

Stephanopolous, et al., "Metabolic engineering methadologies and future prospects," TIB Tech 11:392-396 (1993).

Tan, et al., "Compositional limitations in poly-3-hydroxyalkanoates produced by *Pseudomonas oleovorans*," Journal of Environmental Polymer Degradations 6(2):67 (1998).

Tanahashi & Doi, "Thermal Properties and Stereoregularity of Poly(3-hydroxybutyrate) Prepared from optically Active β-Butyrolactone with a Zinc-Based Catalyst," Macromolecules 24:5732-33 (1991).

Williamson & Engel, "Butyryl-CoA dehydrogenase from *Megasphaera elsdenii*. Specificity of the catalytic reaction," Biochem J. 218(2):521-9 (1984).

Xie, et al., "Ring-opening Polymerization of β—butyrolactone by *Thermophilic lipases*," Macromolecules 30:6997-98 (1997).

Yarlett, et al., "Butyrate formatiion from glucose by the rumen protozoon *Dasytricha ruminantium*," Biochem J. 228(1):187-92 (1985).

Concise Encyclopedia Biochemistry, Second Edition, Ed. Scott and Eagleson, Walter de Gruyter: Berlin-New York., p. 197 (1988).

Doi, et al., "Production of copolyesters of 3-hydroxybutyrate and 3-hydroxyvalerate by *Alcaligenes eutrophus* from butyric and pentanoic acids", *Applied Microbiology and Biotechnology*, 28:330-334 (1988).

Genbank Accession gi: 113527306 (Aug. 2006).

Genbank Accession gi: 73539398 (Dec. 2006).

Haywood, et al, "Characterization of two 3-ketothiolases possessing differing substrate specificities in the polyhydroxyalkanoate synthesizing organism *Alcaligenes eutrophus*", FEMS Microbiology Letters, 52:91-96 (1988).

Kremer, et al., "Biochemical characterization of acyl carrier protein (AcpM) and malonyl-CoA:AcpM transacylase (mtFabD), two major components of *Mycobacterium tuberculosis* fatty acid synthase II", *Jour. Biol. Chem.*, 276(30):27967-27974 (2001).

Slater, et al., "Multiple β-ketothiolases mediate poly(β-hydroxyalkanoate) copolymer synthesis in *Ralstonia eutropha*", *Journal of Bacteriology*, 180(8):1979-1987 (1998).

* cited by examiner

SEQUENCE LISTING

<160> NUMBER OF SEQ ID NOS: 16

<210> SEQ ID NO 1
<211> LENGTH: 34
<212> TYPE: DNA
<213> ORGANISM: Artificial Sequence
<220> FEATURE:
<223> OTHER INFORMATION: Description of Artificial Sequence:
      oligonucleotide primer- RSCP1
<220> FEATURE:
<221> NAME/KEY: misc_feature
<222> LOCATION: (1)..(34)
<223> OTHER INFORMATION: primer

<400> SEQUENCE: 1
gatgccggtc gacccgcggg accgccgctt ctcc         34

```
<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:
      oligonucleotide primer- RSCP2
<220> FEATURE:
<221> NAME/KEY: misc_feature
<222> LOCATION: (1)..(27)
<223> OTHER INFORMATION: primer

<400> SEQUENCE: 2
tcagctgaag acgtacgtac ccggagc                                27

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer- RD-up
<220> FEATURE:
<221> NAME/KEY: misc_feature
<222> LOCATION: (1)..(20)
<223> OTHER INFORMATION: primer
<220> FEATURE:
<221> NAME/KEY: misc_feature
<222> LOCATION: (1)..(20)
<223> OTHER INFORMATION: n represents inosine

<400> SEQUENCE: 3
cgngtngcnc tngtnacngg                                        20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:
      oligonucleotide primer- RD-dwn
<220> FEATURE:
<221> NAME/KEY: misc_feature
<222> LOCATION: (1)..(18)
<223> OTHER INFORMATION: primer
<220> FEATURE:
<221> NAME/KEY: misc_feature
<222> LOCATION: (1)..(20)
<223> OTHER INFORMATION: n represents inosine

<400> SEQUENCE: 4
cccatgtaca gnccnccgtt                                        20

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:
      oligonucleotide primer- C7-5'
<220> FEATURE:
<221> NAME/KEY: misc_feature
<222> LOCATION: (1)..(30)
<223> OTHER INFORMATION: primer

<400> SEQUENCE: 5
aagtcgacca tgcatccgat cggctggggt                             30

<210> SEQ ID NO 6
```

```
<211> LENGTH: 35
<212> TYPE: DNA
<213> ORGANISM: Artificial Sequence
<220> FEATURE:
<223> OTHER INFORMATION: Description of Artificial Sequence:
      oligonucleotide primer- C7-3'
<220> FEATURE:
<221> NAME/KEY: misc_feature
<222> LOCATION: (1)..(35)
<223> OTHER INFORMATION: primer

<400> SEQUENCE: 6
acgctgttca gatcttcgca agatgaatgc taacg                          35

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence:
      oligonucleotide primer- 5' crt
<220> FEATURE:
<221> NAME/KEY: misc_feature
<222> LOCATION: (1)..(47)
<223> OTHER INFORMATION: primer

<400> SEQUENCE: 7
ggggatccga attcaggagg tttttatgga actaaacaat gtcatcc             47

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence:
      oligonucleotide primer- 3' crt
<220> FEATURE:
<221> NAME/KEY: misc_feature
<222> LOCATION: (1)..(31)
<223> OTHER INFORMATION: primer

<400> SEQUENCE: 8
ggaattcgag ctcctatcta tttttgaagc c                              31

<210> SEQ ID NO 9
<211> LENGTH: 47
<212> TYPE: DNA
<213> ORGANISM: Artificial Sequence
<220> FEATURE:
<223> OTHER INFORMATION: Description of Artificial Sequence:
      oligonucleotide primer- 5' hbd
<220> FEATURE:
<221> NAME/KEY: misc_feature
<222> LOCATION: (1)..(47)
<223> OTHER INFORMATION: primer

<400> SEQUENCE: 9
ggaattcggt accaggaggt ttttatgaaa aggtatgtg ttatagg              47

<210> SEQ ID NO 10
<211> LENGTH: 37
<212> TYPE: DNA
<213> ORGANISM: Artificial Sequence
<220> FEATURE:
<223> OTHER INFORMATION: Description of Artificial Sequence:
      oligonucleotide primer-  3' hbd
<220> FEATURE:
<221> NAME/KEY: misc_feature
<222> LOCATION: (1)..(37)
<223> OTHER INFORMATION: primer
```

```
<400> SEQUENCE: 10
ggaattcccc gggttatttt gaataatcgt agaaacc                                37

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence:
      oligonucleotide primer- 5' bcd
<220> FEATURE:
<221> NAME/KEY: misc_feature
<222> LOCATION: (1)..(45)
<223> OTHER INFORMATION: primer

<400> SEQUENCE: 11
ggaattcctg cagaggaggt tttatggatt ttaatttaac aagag                       45

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence:
      oligonucleotide primer-  3' bcd
<220> FEATURE:
<221> NAME/KEY: misc_feature
<222> LOCATION: (1)..(33)
<223> OTHER INFORMATION: primer

<400> SEQUENCE: 12
ggaattcgca tgcttatcta aaattttc ctg                                       33

<210> SEQ ID NO 13
<211> LENGTH: 54
<212> TYPE: DNA
<213> ORGANISM: Artificial Sequence
<220> FEATURE:
<223> OTHER INFORMATION: Description of Artificial Sequence:
      oligonucleotide primer- 5' eftBA
<220> FEATURE:
<221> NAME/KEY: misc_feature
<222> LOCATION: (1)..(54)
<223> OTHER INFORMATION: primer

<400> SEQUENCE: 13
ggaattcgga tccaggaggt tttatgaata tagttgtttg tttaaacaag ttcc             54

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:
      oligonucleotide primer-  3' eftBA
<220> FEATURE:
<221> NAME/KEY: misc_feature
<222> LOCATION: (1)..(40)
<223> OTHER INFORMATION: primer

<400> SEQUENCE: 14
ggaattcgtc gacttaatta ttagcagctt taacttgagc                             40

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence:
```

-continued

```
        oligonucleotide primer- Ac3-5'
<220> FEATURE:
<221> NAME/KEY: misc_feature
<222> LOCATION: (1)..(39)
<223> OTHER INFORMATION: primer

<400> SEQUENCE: 15
agaattcagg aggacgccgc atgagcgcac aatccctgg                              39

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:
        oligonucleotide primer- Ac3-3'
<220> FEATURE:
<221> NAME/KEY: misc_feature
<222> LOCATION: (1)..(29)
<223> OTHER INFORMATION: primer

<400> SEQUENCE: 16
ttcctgcagc tcaaggcagc ttgaccacg                                         29
```

TRANSGENIC SYSTEMS FOR THE MANUFACTURE OF POLY(2-HYDROXY-BUTYRATE-CO-3-HYDROXYHEXANOATE)

CROSS-REFERENCE TO RELATED APPLICATIONS

This application is a continuation of Ser. No. 09/235,875 filed Jan. 22, 1999 which claims priority to U.S. Provisional Application Ser. No. 60/072,198 filed Jan. 22, 1998.

BACKGROUND OF THE INVENTION

The present invention is generally in the field of polyhydroxyalkanoate materials, and more particularly to improved methods of production thereof Polyhydroxyalkanoates (PHAs) are natural, thermoplastic polyesters and can be processed by traditional polymer techniques for use in an enormous variety of applications, including consumer packaging, disposable diaper linings and garbage bags, food and medical products. Methods which can be used for producing PHA polymers from microorganisms which naturally produce polyhydroxyalkanoates are described in U.S. Pat. No. 4,910,145 to Holmes, et al.; Byrom, "Miscellaneous Biomaterials" in Biomaterials (Byrom, ed.) pp. 333-59 (MacMillan Publishers, London 1991); Hocking and Marchessault, "Biopolyesters" in Chemistry and Technology of Biodegradable Polymers (Griffin, ed.) pp. 48-96 (Chapman & Hall, London 1994); Holmes, "Biologically Produced (R)-3-hydroxyalkanoate Polymers and Copolymers" in Developments in Crystalline Polymers (Bassett, ed.) vol. 2, pp. 1-65 (Elsevier, London 1988); Lafferty et al., "Microbial Production of Poly-b-hydroxybutyric acid" in Biotechnology (Rehm & Reed, eds.) vol. 66, pp. 135-76 (Verlagsgesellschaft, Weinheim 1988); Müiller & Seebach, Angew. Chem. Int. Ed. Engl. 32:477-502 (1993). The natural biosynthetic pathway for production of polyhydroxybutyrate (PHB) is shown in FIG. 1.

Methods for producing PHAs in natural or genetically engineered organisms are described by Steinbüchel, "Polyhydroxyalkanoic Acids" in Biomaterials (Byrom, ed.) pp. 123-213 (MacMillan Publishers, London 1991); Williams & Peoples, CHEMTECH, 26:38-44 (1996); Steinbüchel & Wiese, Appl. Microbiol. Biotechnol., 37:691-97 (1992); U.S. Pat. Nos. 5,245,023; 5,250,430; 5,480,794; 5,512,669; 5,534,432 to Peoples and Sinskey (which also disclose and claim the genes encoding reductase, thiolase, and PHB polymerase); Agostini et al., Polym. Sci., Part A-1, 9:2775-87 (1971); Gross et al., Macromolecules, 21:2657-68 (1988); Dubois, et al., Macromolecules, 26:4407-12 (1993); Le Borgne & Spassky, Polymer, 30:2312-19 (1989); Tanahashi & Doi, Macromolecules, 24:5732-33 (1991); Hori et al., Macromolecules, 26:4388-90 (1993); Kemnitzer et al., Macromolecules, 26:1221-29 (1993); Hori et al., Macromolecules, 26:5533-34 (1993); Hocking & Marchessault, Polym. Bull., 30:163-70 (1993); Xie et al., Macromolecules, 30:6997-98 (1997); and U.S. Pat. No. 5,563,239 to Hubbs et al. A general pathway for production of PHAs is shown in FIG. 2. Synthetic polymer synthesis approaches including direct condensation and ring-opening polymerization of the corresponding lactones are described in Jesudason & Marchessault, Macromolecules 27:2595-602 (1994); U.S. Pat. No. 5,286,842 to Kimura; U.S. Pat. No. 5,563,239 to Hubbs et al.; U.S. Pat. No. 5,516,883 to Hori et al.; U.S. Pat. No. 5,461,139 to Gonda et al.; and Canadian Patent Application No. 2,006,508. WO 95/15260 describes the manufacture of poly(3hydroxybutyrate-co-3-hydroxyvalerate) (PHBV) films, and U.S. Pat. Nos. 4,826,493 and 4,880,592 to Martini et al. describe the manufacture of PHB and PHBV films. U.S. Pat. No. 5,292,860 to Shiotani et al. describes the manufacture of the PHA copolymer poly(3-hydroxybutyrate-co-3hydroxyhexanoate) (PHBHH).

To date, PHAs have seen limited commercial availability, with only the copolymer PHBV being available in development quantities. This copolymer has been produced by fermentation of the bacterium Ralstonia eutropha. Fermentation processes for production of other PHAs have been developed (Williams & Peoples, CHEMTECH 26: 38-44 (1996)). Plant crops are also being genetically engineered to produce these polymers, offering a cost structure in line with the vegetable oils and direct price competitiveness with petroleum-based polymers (Williams & Peoples, CHEMTECH 26: 38-44 (1996)).

Several factors are critical for economic biological production of PHAs, including substrate costs, fermentation time, and efficiency of downstream processing. For large-scale fermentations of commodity products, it is generally known that plasmid-based systems are unsatisfactory due to the extra burden of maintaining the plasmids and problems in maintaining stable expression.

Known biological systems for the production of PHAs containing 3hydroxy-co-hydroxyhexanoate (3H-co-HH) are inefficient. For example, Shimamura, et al., Macromolecules, 27:878 (1994) discloses that Aeromonas caviae synthesizes a PHA composed of 3-hydroxybutyrate and 3hydroxyhexanoate (3HH) when grown on olive oil or $C_{12}$ to $C_{18}$ fatty acids. The fraction of the 3HH monomer was determined to be dependent on the concentration of the carbon source and the fermentation time and could amount to levels of 25% (Doi, et al., Macromolecules, 28: 4822 (1995)). As a result of increasing 3HH substrate levels, the crystallinity, melting temperature, and glass-transition temperature of the PHA decrease. These changes in physical properties lead to an increased susceptibility to degradation by PHB depolymerase from Alcaligenes faecalis. Other natural microorganism that incorporate low levels of 3HH in a PHB copolymer are Comamonas testosteroni and Bacillus cereus (Huisman, et al., Appl. Environ. Microbiol. 55: 1949 (1989); Caballero, et al., Int. J. Biol. Macromol., 17: 86 (1995)). Recombinant Pseudomonas putida GPp104 strains in which the phb genes from either Thiocapsia pfenigii or Chromatium vinosum were introduced also accumulated PHA with 3-hydroxyhexanoate as major constituent.

PHAs generally are divided into two classes based on the polymer composition: short side-chain PHAs and long side-chain PHAs. Incorporation of monomers from one group into a PHA belonging to the other usually is limited to low levels. In some cases where the monomers are abundant for both PHAs, the bacterium generally produces separate PHA granules each comprising one type of PHA. Substrate specificities of the PHA polymerases therefore can be generalized as optimal for short side-chains ($C_4$ and $C_5$) or medium side-chains ($C_8$-$C_{10}$). Based on composition of PHAs synthesized by individual microorganisms, PHA polymerases that incorporate 3-hydroxyhexanoate can be identified. Thus, PHA polymerases from A. caviae, C. testosteroni and T. pfenigii are known for incorporating 3-hydroxyhexanoate into the PHA, whereas the enzymes from Paracoccus denitrificans, Sphaerotilus natans and Rhodococcus sp. have a preference for 3-hydroxyvalerate. The PHA polymerases from the latter organisms also are useful in making PHB-co-HH copolymers, due to their preference for $C_5$ over $C_4$. Unfortunately, however, these bacteria generally have a low growth rate, often are difficult to break open, and have only a limited amenability to genetic engineering. It is thus desirable to develop efficient, more cost-effective ways of producing PHAs containing 3H-co-HH by biological systems.

It is therefore an object of the present invention to provide genetically engineered systems for the production of polyhydroxyalkanoate polymers including 3-hydroxyhexanoate monomers (HHPHA).

It is another object of this invention to provide useful mutations which can be used to produce 3-hydroxyhexanoic monomers from more economic feedstocks, such as butyrate or butanol.

It is a further object of this invention to provide genes suitable for converting cellular metabolites derived from carbohydrate feedstocks to Butyryl-CoA for the production of 3-hydroxyhexanoate comonomers.

It is another object of this invention to provide improved methods of producing PHAs containing 3-hydroxyhexanoate as comonomer.

It is still another object of this invention to provide new pathways in biological systems for the endogenous synthesis of the 3-hydroxyhexanoate monomer.

It is a further object of this invention to provide genetically engineered biological systems for production of PHAs containing 3-hydroxyhexanoate in which expression is sufficient and stable.

SUMMARY OF THE INVENTION

It has been discovered that biological systems for the production of PHAs containing 3-hydroxy-co-hydroxyhexanoate (3H-co-HH) can be improved by using transgenic organisms with faster growth rates and/or by genetically engineering these organisms to produce the co-monomer 3-hydroxyhexanoic acid from cheaper feedstocks, such as butyrate or butanol, or directly from glucose by incorporating genes encoding enzymes which can channel cellular intermediates to butyryl-CoA, thereby improving the economics of PHA production using transgenic organisms. These processes are based on genetically engineered bacteria such as Escherichia coli or on plant crops as production systems which include PHA biosynthetic genes from PHA producers such as R. eutropha and P. putida. In a preferred embodiment of the method, additional genes are introduced in transgenic PHB producers, thereby creating new strains that synthesize monomers such as 3HH which are incorporated into PHAs.

In a preferred embodiment of the methods, microorganisms which do not normally produce the storage polymer PHAs are genetically engineered to produce PHAs by the introduction of a PHA synthase gene and additional transgenes selected from the group comprising genes encoding β-ketothiolase, acetoacetyl-CoA reductase, β-ketoacyl-CoA reductase, enoyl-CoA hydratase and B-hydroxyacyl-ACP-coenzymeA transferase. The genes are preferably selected on the basis of the substrate specificity of their encoded enzymes being beneficial for the production of the 3HH polymers. Useful mutations that can be used to produce 3-hydroxyhexanoic monomers from more economic feedstocks, such as butyrate or butanol, are described. These mutants can be readily generated in bacteria suitable for practising the described invention by standard techniques known to those skilled in the art.

Methods for engineering transgenic organisms that synthesize PHAs containing 3-hydroxyhexanoate as comonomer have been developed. In a preferred embodiment of these systems, the method is used to engineer either (1) a bacterium such as Escherichia coli, Klebsiella, Ralstonia eutropha, Alcaligenes latus, Pseudomonas putida or other microorganisms that are able to synthesize PHAs, or (2) a higher plant, such as the seed of an oil crop (e.g., Brassica, sunflower, soybean, corn, safflower, flax, palm or coconut) or starch accumulating plants (e.g., potato, tapioca, or cassava). These are screened to identify enzyme activities desirable for conversion of metabolic intermediates into R-3-hydroxyhexanoyl CoA, specifically butyryl CoA dehydrogenase activity and acyl CoA:ACP transferase activities. The latter conversion is catalyzed either by a single protein or by a combination of thioesterase and acyl CoA synthase activities. The flux of normal cellular metabolites to 3-hydroxyhexanoate is redirected via one or more of three different pathways. These three pathways generate 3-hydroxyhexanoate, either (1) using a butyrate fermentation pathway from Clostridium acetobutylicum, (2) using fatty acid biosynthetic enzymes from E. coli, or (3) using the fatty acid oxidation complex from Pseudomonas putida. Examples demonstrate a bacterium expressing a functional PHA synthase from a transgene is described, along with methods for expressing these genes in transgenic plant crops.

Methods to select genes that encode enzymes which convert crotonyl CoA to butyryl CoA are provided, as well as screening methods that identify enzymes that convert acyl ACP intermediates into acyl CoA or into acyl CoA precursors for PHA biosynthesis. Transgenic E. coli strains in which a gene encoding a PHA polymerase is integrated in the chromosome and expressed to levels supporting PHA synthesis are provided. Such transgenic strains, which also have specific mutations on the chromosome, allow the selection and screening of these activities using genomic libraries from different biological sources.

Procedures are described for engineering new pathways in biological systems for the endogenous synthesis of the 3-hydroxyhexanoate monomer. In a preferred embodiment, E. coli is engineered to synthesize PHBH from either inexpensive carbohydrate feedstocks such as glucose, sucrose, xylose and lactose or mixtures of such carbohydrates and fatty acids as the only carbon source by introducing genes encoding enzymes that convert cellular metabolites to 3-hydroxyhexanoyl CoA into the E. coli. For efficient PHA synthesis in recombinant E. coli strains, it is crucial that the expression of all the genes involved in the pathway be adequate. To this end, the genes of interest can be expressed from extrachromosomal DNA molecules such as plasmids, which intrinsically results in a copy-number effect and consequently high expression levels, or they can be expressed from the chromosome. For large-scale fermentations of commodity products it is generally known that plasmid-based systems are unsatisfactory due to the extra burden of maintaining the plasmids and the problems of stable expression. These drawbacks can be overcome using chromosomally encoded enzymes and/or by improving the transcriptional and translational signals preceding the gene of interest such that expression is sufficient and stable.

DETAILED DESCRIPTION OF THE INVENTION

Figure 1:
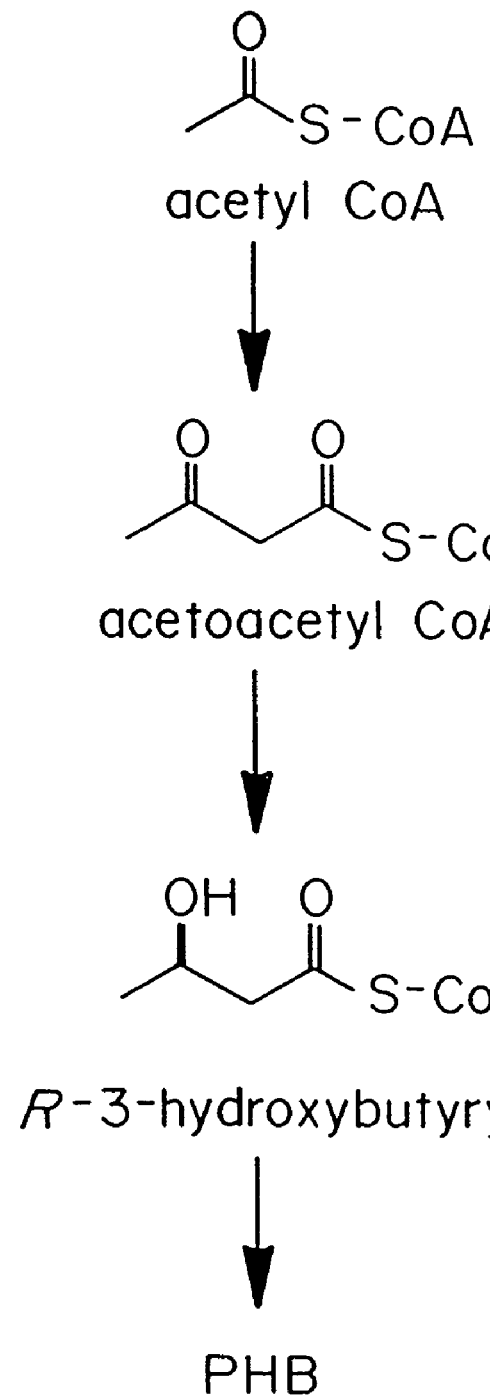
FIG. 1 is a schematic of a pathway for biosynthesis of PHB.
Figure 2:
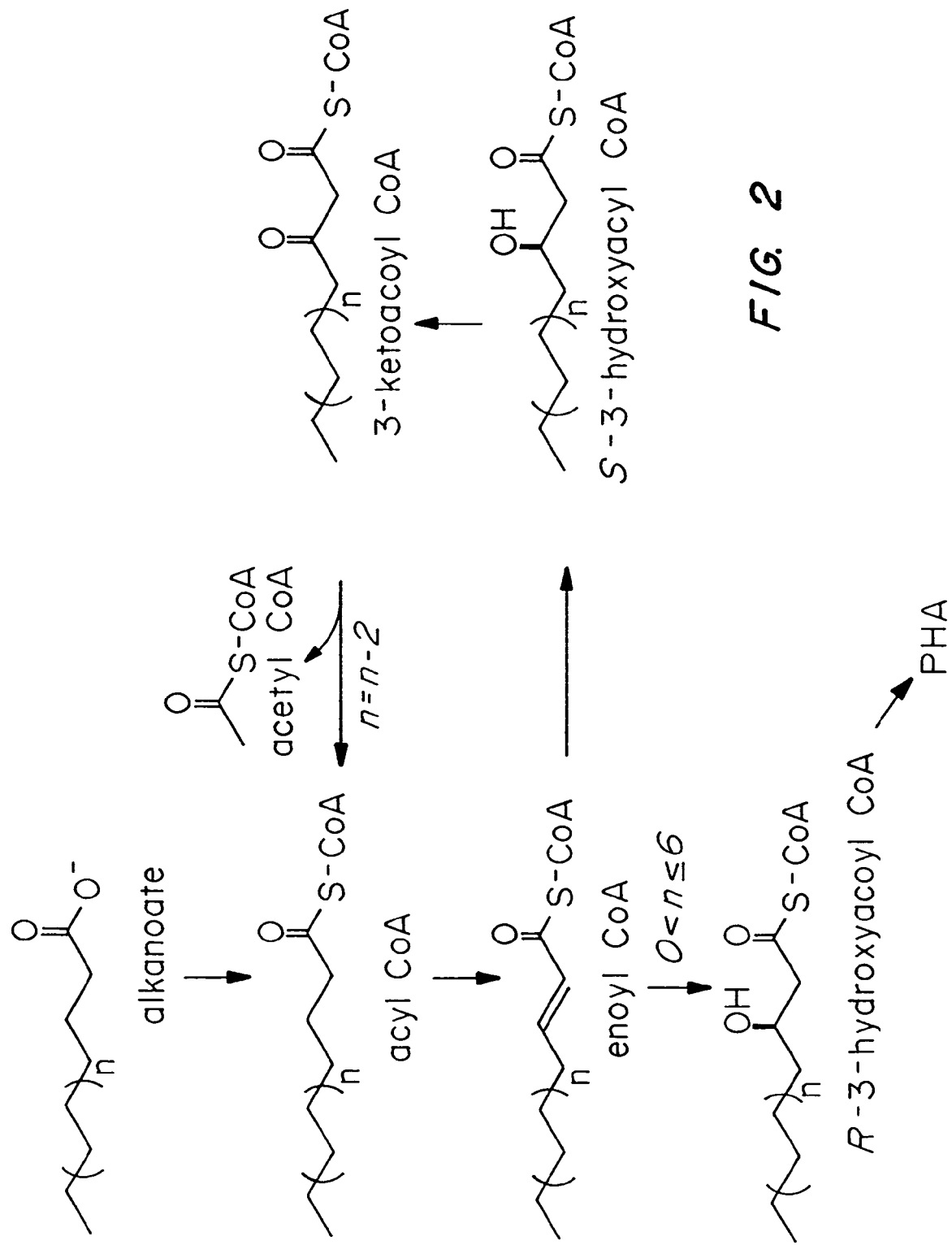
FIG. 2 is a schematic of a general pathway for biosynthesis of PHA.

Metabolism of any HA production organism, including bacteria and plant crops, can be redirected to supply specific metabolites for PHA synthesis by metabolic engineering. In order to make this approach effective, it is necessary to develop new biochemical pathways leading to the desired monomer from common metabolic intermediates. It is not necessary that such pathways exist in one organism as the individual steps can be reconstituted in the production organism of choice using genetic engineering techniques. Processes developed to incorporate alternative monomers that are derived from supplemented feedstocks have specific drawbacks. First, adding supplemental feeds into a fermenter are costly as they expand the infrastructure and impose additional quality control. Second, addition of monomer precursors in the feed needs to be tightly controlled to achieve a constant composition of the monomer pools and PHA composition.

A similar approach in metabolic engineering methods have therefore been developed which allow production of PHBH in organisms, such as *R. eutropha, C. Testosteroni, A. latus, A. vinelandii* and *P. denitrificans*, as well as in transgenic microbial and plant crop systems expressing a PHA synthase from a heterologous gene or genes.

I. Polyhydroxyalkanoates

Several types of PHAs are known. It is useful to broadly divide the PHAs into two groups according to the length of their side chains and according to their pathways for biosynthesis. Those with short side chains, such as polyhydroxybutyrate (PHB), a homopolymer of R-3-hydroxybutyric acid units, are crystalline thermoplastics; PHAs with long side chains are more elastomeric. The former polymers have been known for about seventy years (Lemoigne & Roukhelman 1925), while the latter polymers are a relatively recent discovery (deSmet, et al., *J. Bacteriol.*, 154:870-78 (1983)). Before this designation, however, PHAs of microbial origin containing both R-3-hydroxybutyric acid units and longer side chain units from C5 to C16 were identified (Wallen & Rowheder, *Environ. Sci. Technol.*, 8:576-79 (1974)). A number of bacteria which produce copolymers of D-3-hydroxybutyric acid and one or more long side chain hydroxyacid units containing from five to sixteen carbon atoms have been identified more recently (Steinbüchel & Wiese, *Appl. Microbiol. Biotechnol.*, 37:691-97 (1992); Valentin et al., *Appl. Microbiol. Biotechnol.*, 36: 507-14 (1992); Valentin et al., *Appl. Microbiol. Biotechnol.*, 40:710-16 (1994); Abe et al., *Int. J. Biol. Macromol.*, 16:115-19 (1994); Lee et al., *Appl. Microbiol. Biotechnol.*, 42:901-09 (1995); Kato et al., *Appl. Microbiol. Biotechnol.*, 45:363-70 (1996); Valentin et al., *Appl. Microbiol. Biotechnol.*, 46:261-67 (1996); U.S. Pat. No. 4,876,331 to Doi). Useful examples of specific two-component copolymers include PHB-co-3-hydroxyhexanoate (Brandl et al., *Int. J. Biol. Macromol.*, 11:49-55 (1989); Amos & McInerey, *Arch. Microbiol*, 155:103-06 (1991); U.S. Pat. No. 5,292,860 to Shiotani et al.). Other representative PHAs are described in Steinbüchel & Valentin, *FEMS Microbiol. Lett.*, 128:219-28 (1995). Chemical synthetic methods have also been applied to prepare racemic PHB copolymers of this type for applications testing (PCT WO 95/20614, PCT WO 95/20615, and PCT WO 96/20621).

Useful molecular weights of the polymers are between about 10,000 and 4 million Daltons, and preferably between about 50,000 and 1.5 million Daltons. The PHAs preferably contain one or more units of the following formula:

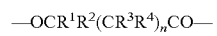

wherein n is 0 or an integer; and wherein $R^1$, $R^2$, $R^3$, and $R^4$ are independently selected from saturated and unsaturated hydrocarbon radicals, halo- and hydroxy- substituted radicals, hydroxy radicals, halogen radicals, nitrogen-substituted radicals, oxygen-substituted radicals, and hydrogen atoms.

Monomeric units generally include hydroxybutyrate, hydroxyvalerate, hydroxyhexanoate, hydroxyheptanoate, hydroxyoctanoate, hydroxynonanoate, hydroxydecanoate, hydroxyundecanoate, and hydroxydodecanoate units. PHAs can include monomers and polymers and derivatives of 3-hydroxyacids, 4-hydroxyacids and 5-hydroxyacids.

II. Methods of Preparing Polyhydroxyalkanoates

The PHAs can be prepared from a biological source such as a microorganism which naturally produces PHAs and which can be induced to produce the desired PHAs by manipulation of culture conditions and feedstocks, these or other microorganisms genetically engineered as described herein, or higher organisms, such as plants, which have been genetically engineered to produce PHAs.

Substrate Specificity of the Enzymes Required for PHA Synthesis

Suitable sources of PHA synthase genes are readily identified by analyzing the compositions of PHAs produce when grown on fatty acids and then isolating the PHA synthase genes by methods well known to those skilled in the art. Useful PHA synthase genes have been isolated from, for example, *Aeromonas caviae* (Fukui & Doi, J Bacteriol. 179: 4821-30 (1997)), *Rhodospirillum rubrum* (U.S. Pat. No. 5,849,894), *Rhodococcus ruber* (Pieper & Steinbuechel, *FEMS Microbiol.Lett.* 96(1): 73-80 (1992)), and *Nocardia corallina* (Hall et. al., *Can. J. Microbiol.* 44: 687-91 (1998)).

In vitro studies on PHB polymerases have shown that the enzyme from *Z. ramigera* I-1 6-M is strictly specific for the R-isomer of 3-hydroxy-butyryl CoA (Fukui, et al., *Arch. Microbiol.*, 110: 149 (1976)). The PHB polymerase from *R. eutropha* is highly specific for the 3-hydroxybutyryl CoA monomer and shows only 7.5% activity towards 3-hydroxyvaleryl CoA. No activity with 3hydroxyhexanoyl CoA or longer 3-hydroxyacyl CoA's was detected in in vitro studies (Haywood, et al., *FEMS Microhiol. Lett.*, 57:1 (1989)).

The NADPH-linked acetoacetyl CoA reductase from Z. ramigera is most active with acetoacetyl CoA, whereas 3-ketovaleryl CoA (41% of the maximal. activity) and 3-ketohexanoyl CoA (0.6%) were also substrates for the enzyme (Ploux, et al. *Eur. J. Biochem.*, 174: 177 (1988)). In *R. eutropha*, the reductase activities for 3-ketovaleryl CoA and 3-ketohexanoyl CoA are respectively 48% and 3.6% of the activity that was determined for acetoacetyl CoA (Haywood, et al.,

*FEMS Microbiol. Lett.*, 52:259 (1988)). In addition, *R. eutropha* has an NADH-dependent activity towards S-3-hydroxyacyl CoA's which is highest for the $C_4$ and $C_8$ substrates.

*R. eutropha* also has two 3-ketothiolases (A and B) which have the highest activity towards the acetoacetyl CoA substrates and only 3% of the maximal activity towards 3-ketovaleryl CoA (Haywood, et al., *FEMS Microbiol. Lett.*, 52:91 (1988)). While enzyme A is 10 times more active and strictly specific for these two substrates, enzyme B also has 1-2% activity for the higher 3-ketoacyl CoA's.

In summary, the synthesis of 3-hydroxyhexanoyl-CoA monomers with the PHB enzymes from *R. eutropha* or *Z. ramigera* can be improved by identifying and using thiolase and/or reductase genes with advantageous substrate specificity for 3-ketohexanoyl-CoA. It is therefore necessary to identify and isolate genes encoding activities that can supply 3-hydroxyhexanoyl CoA for PHA biosynthesis.

Identification and Isolation of Phb Genes from *Nocardia salmonicolor*.

*N. salmonicolor* is a member of the genus Rhodococcus which is known to incorporate high levels of 3-hydroxyvalerate into PHAs when grown on simple sugars as carbon source. This characteristic suggests that the PHB biosynthetic enzymes from *N. salmonicolor* are likely to have a wider substrate range than other PHB biosynthetic enzymes, such as those from *R. eutropha*. The genes encoding PHB polymerase and acetoacetyl CoA reductase were amplified by polymerase chain reaction using primers that were based on the nucleotide sequence of the phaC gene from *Rhodococcus ruber* and conserved regions in the N- and C-terminal ends of known acetoacetyl CoA dehydrogenases. DNA fragments containing the phbB and phbC genes from *N. salmonicolor* were identified in genomic digests by Southern blotting using the corresponding PCR products as probes. A 3.6 kb BamHI (phbC) and 4.2 kb PvuII (phbB) fragment were cloned into pUC119 and identified by colony blotting using the corresponding PCR products as probes.

Endogenous Formation of R-3-Hydroxyhexanoyl CoA Using the Butyrate Fermentation Pathway from *Clostridium acetobutylicum*.

Figure 3:
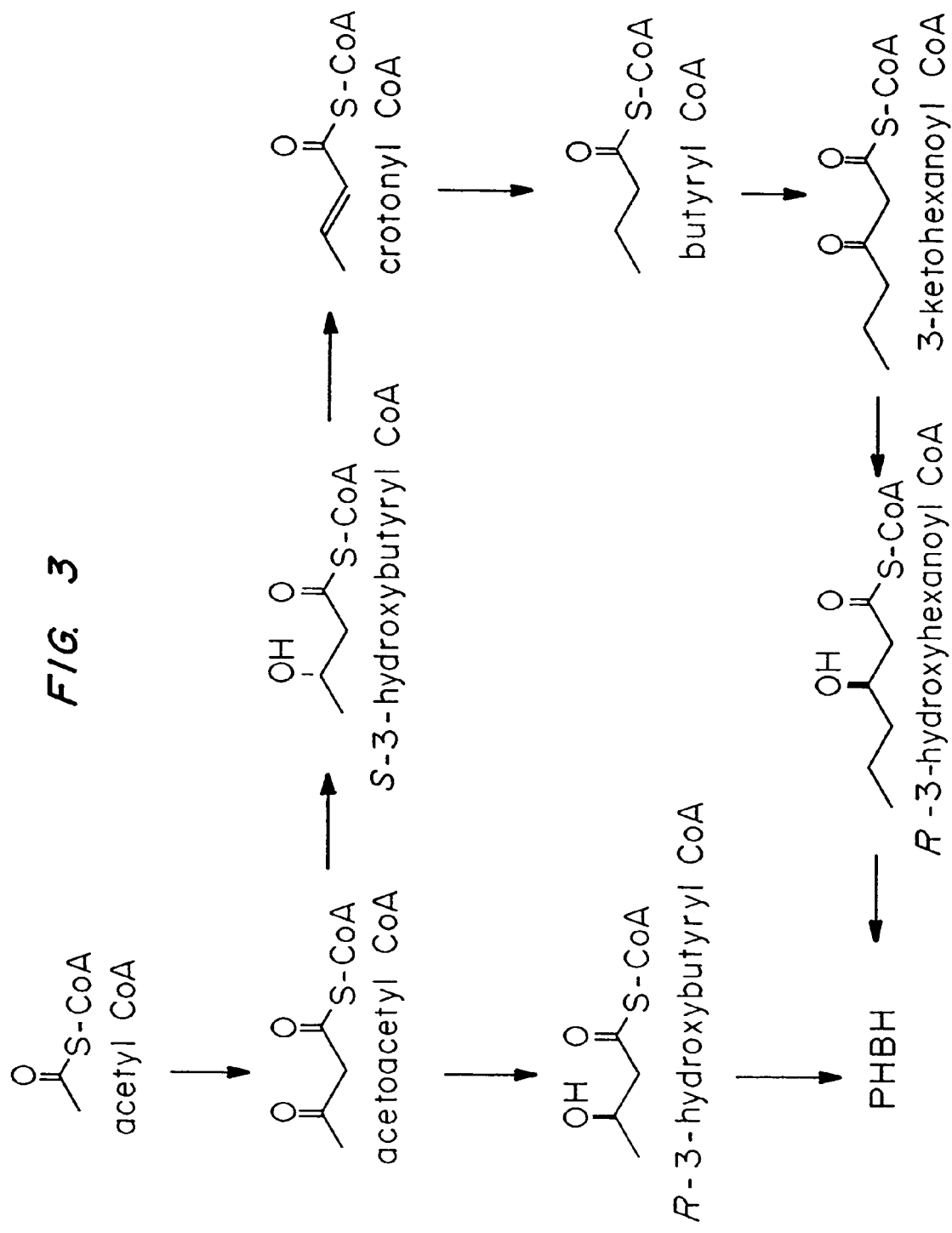
FIG. 3 is a schematic of a preferred pathway for biosynthesis of PHBH using the Clostridium acetbutylicum butyrate fermentation pathway.

A biosynthetic pathway that results in R-3-hydroxyhexanoyl CoA formation involves the elongation of butyryl CoA to 3-ketohexanoyl CoA which can subsequently be reduced to the monomer precursor, as shown in FIG. 3. Butyryl CoA is formed by butyrate fermenting organisms such as *C. acetobutylicum* in a four step pathway from acetyl CoA. Elongation of butyryl CoA to 3-ketohexanoyl CoA is catalyzed by a thiolase. The complete pathway thus involves (1) the PHB biosynthetic thiolase, (2) the three enzymes from *C. acetobutylicum* that form butyryl CoA, (3) a second thiolase, specific for 3-ketohexanoyl CoA, (4) a reductase specific for this substrate, and (5) a PHB polymerase that accepts both 3-hydroxybutyryl CoA and 3-hydroxyhexanoyl CoA.

The *C. acetobutylicum* locus involved in butyrate fermentation encodes 5 enzymes/proteins: crotonase (crt), butyryl CoA dehydrogenase (bca), 2 ETF proteins for electron transport (etfA and etfB), and 3-hydroxybutyryl CoA dehydrogenase (hbd) (Boynton et al., *J. Bacteriol.* 178:3015 (1996)). Another microorganism from which these genes have been isolated is *Thermoanaerobacterium thermosaccharolyticum* (van Rinsum, GenBank Acc. no.). Hbd and crt have been isolated from *C. difficile* as well (Mullany et al., *FEMS Microbiol.* Lett. 124:61 (1994)). 3-hydroxybutyryl CoA dehydrogenase activity has been detected in *Dastricha ruminatium* (Yarlett et al., *Biochem. J.* 228:187 (1995)), *Butyrivibrio fibrisolvens* (Miller & Jenesel, *J. Bacteriol.*, 138:99 (1979)), *Treponema phagedemes* (George & Smibert, *J. Bacteriol.,* 152:1049 (1982)), *Acidaminococcus fermentans* (Hartel & Buckel, *Arch. Microbiol.,* 166:350 (1996)), *Clostridium kluyveri* (Madan et al., *Eur. J. Biochem.*, 32:51 (1973)), *Syntrophospora bryanti* (Dong & Stams, *Antonie van Leeuwenhoek,* 67:345 (1995)); crotonase activity has been detected in *Butyrivibrio fibrisolvens* (Miller & Jenesel, *J. Bacteriol.*, 138:99 (1979)); and butyryl CoA dehydrogenase activity has been detected in Megasphaera elsdenii (Williamson & Engel, *Biochem. J.,* 218:521 (1984)), *Peptostreptococcus elsdenii* (Engel & Massay, *Biochem. J.*, 1971, 125:879), *Syntrophospora bryanti* (Dong & Stams, *Antonie van Leeuwenhoek,* 67:345 (1995)), and *Treponema phagedemes* (George & Smibert, *J. Bacteriol.,* 152:1049 (1982)).

For all CoA-involving thiolases known so far the reaction primarily proceeds in the catabolic direction. Also, the thiolase encoded byphbA preferably degrades acetoacetyl CoA. Thus, in a biosynthetic pathway to 3-ketohexanoyl CoA a catabolic thiolase can be used if the reaction is being pulled in the anabolic direction by a reductase and PHA polymerase. Besides the known PHB thiolases, genes encoding these enzymes can be obtained from a range of bacteria, mammals and plants. In fact, *E. coli* has five thiolases that have been characterized poorly, both biochemically and physiologically. Two of these thiolases are encoded by previously identified genes, fadA and atoB, whereas three others are encoded by open reading frames that have not been studied. These thiolases were overexpressed and assayed with different substrates in vitro assays. Reductase and polymerase genes are taken from *N. salmonicolor* or any other PHA producer that incorporates $C_6$ monomers.

Endogenous Formation of R-3-hydroxyhexanoyl CoA Via the Fatty Acid Oxidation Pathway.

Figure 4:
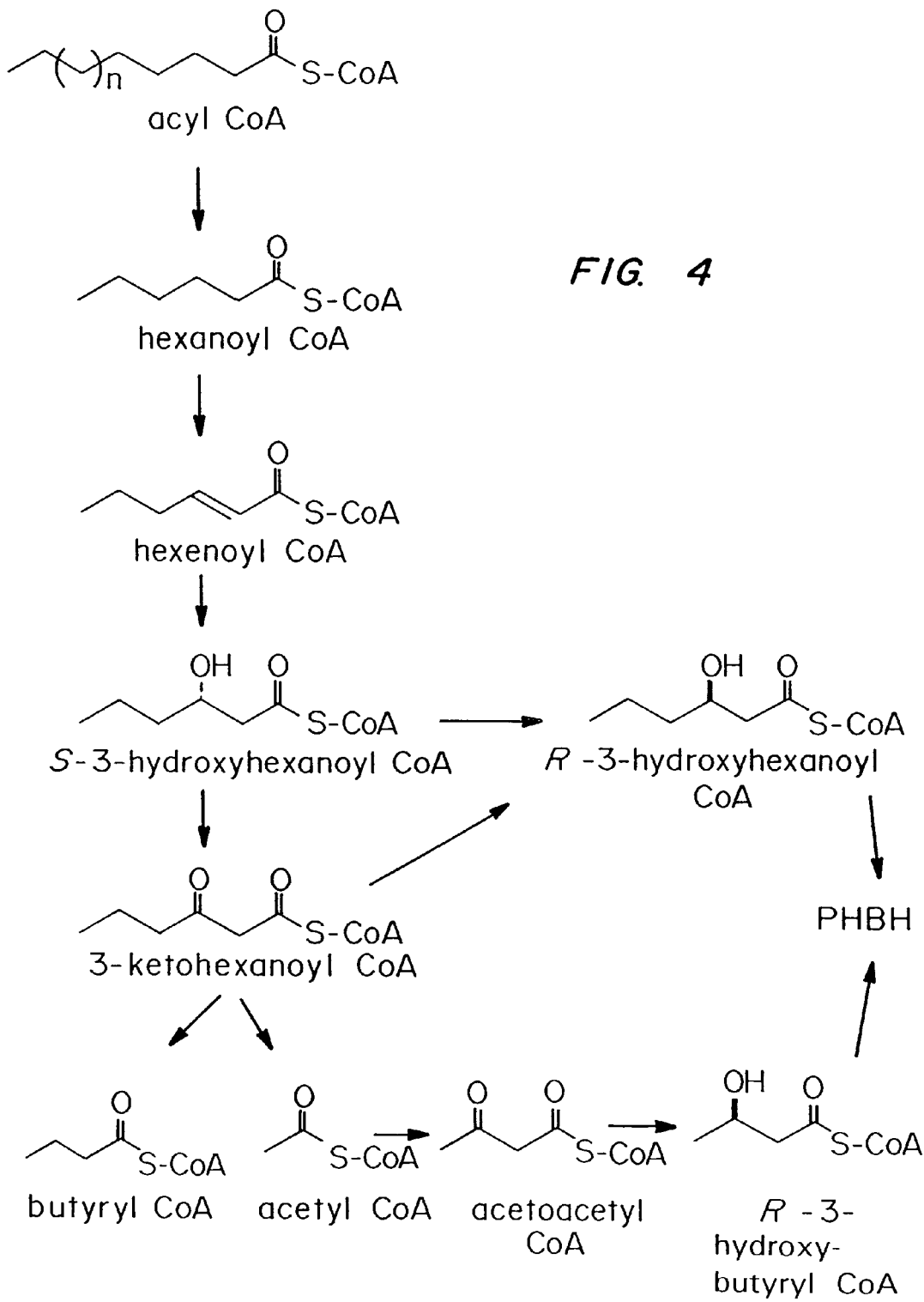
FIG. 4 is a schematic of a preferred pathway for biosynthesis of PHBH using the fatty acid oxidation pathway.

In *P. putida* monomers for PHA biosynthesis are derived from the fatty acid oxidation pathway when alkanes or oxidized alkanes are provided as carbon and energy source. The intermediate in this pathway that is channeled to PHA biosynthesis is postulated to be S-3-hydroxyacyl CoA (preferentially $C_8$ and $C_{10}$) which undergoes epimerization by the FaoAB complex to the R-isomer. The combined action of epimerase and PHA polymerase provides $C_6$ to $C_{14}$ monomers for PHA. Consequently, a combination of this epimerase and a 3-hydroxyhexanoyl CoA accepting PHA polymerase provides the biosynthetic capability to synthesize PHBH from fatty acids in transgenic organisms, as shown by FIG. 4. Mixtures of fatty acids and carbohydrates that are useful feedstocks for fermentative production as the 3 HB monomer can be derived from acetyl CoA, whereas the 3HH component is from fatty acids. For plant crops, synthesis of the 3-hydroxyhexanoate monomer proceeds anabolically from acetyl-CoA, or catabolically from fatty acids.

Epimerase activity has been detected in the fatty acid oxidation complexes from *E. coli* (FadAB) (Pramanik et al., *J. Bateriol.* 137:469 (1979)) and *P. fragi* FaoAB (Imamura et al., *J. Biochem.* 107: 184 (1990)). The FaoAB complex from *P. putida* KT2442 was examined after the subunits were cloned in the overexpression vector pTrcN and this complex demonstrated epimerase activity towards 3-hydroxyoctanoyl CoA, limited activity towards 3hydroxybutyryl CoA and hardly detectable levels towards 3-hydroxyoctanoyl CoA. These results suggest that the FaoAB complex may be a determining factor in the substrate specificity of the PHA pathway in P. putida. Consequently, FaoAB complexes from other sources can be used to generate novel 3-hydroxyacyl CoA pools in recombinant organisms, prokaryotic, eukaryotic or archaeic. Homologous genes are readily isolated from bacteria such a *R. eutropha, A. latus, C. testosteroni, P. denitrificans, R. ruber* and other PHA and non-PHA producers using the same methods to identify the faoAB genes in *P. putida* KT2442.

Endogenous Formation of R-3-hydroxyoctanoyl CoA Via the Fatty Acid Biosynthetic Pathway.

Figure 5:
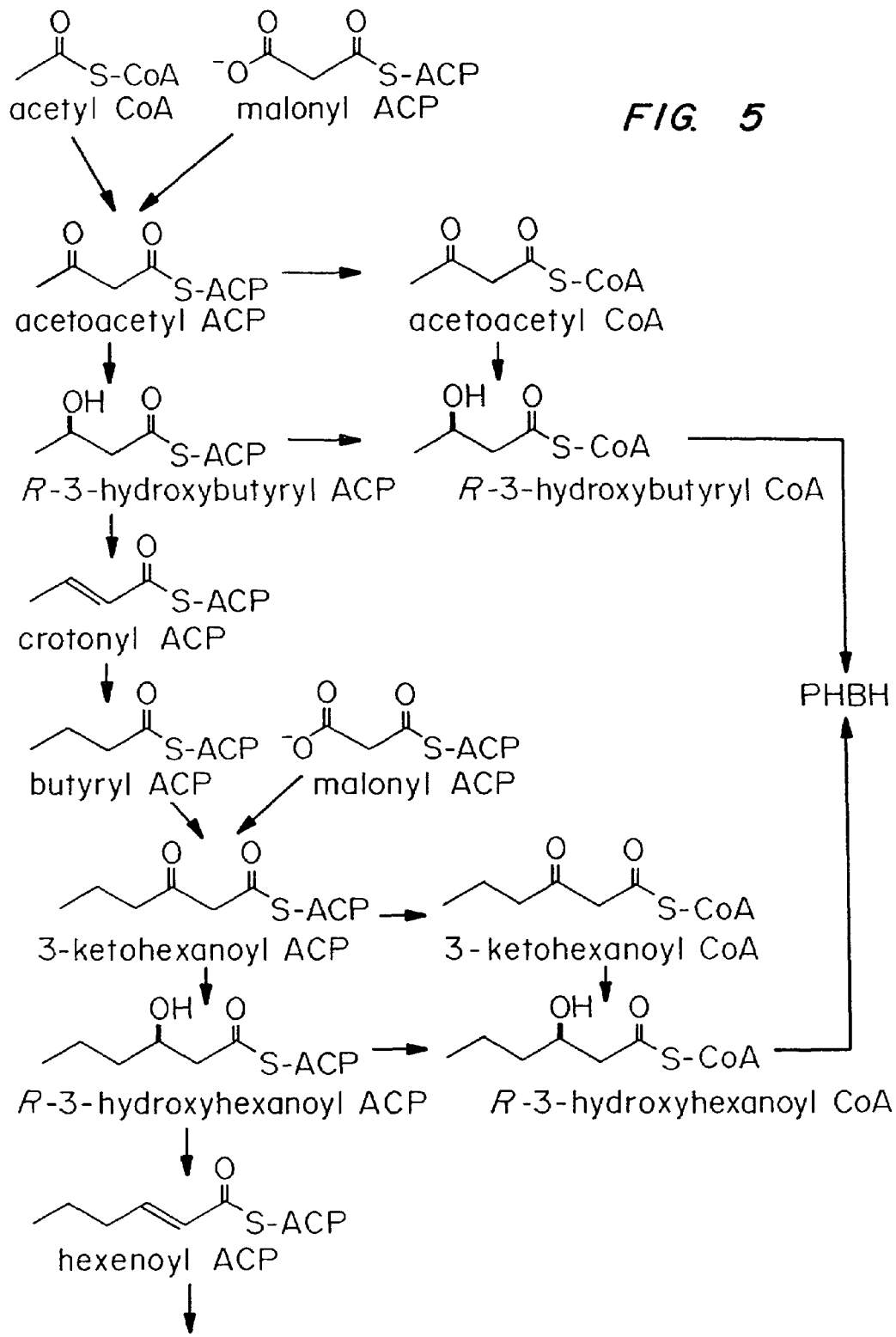
FIG. 5 is a schematic of a preferred pathway for biosynthesis of PHBH using the fatty acid pathway.

*P. putida* and *P. aeruginosa* synthesize PHAs composed of medium-chain length 3-hydroxy fatty acids when grown on sugars. The predominant monomer in these PHAs is 3-hydoxydecanoate. A similar pathway can be engineered for the synthesis of PHBH in either recombinant microorganisms such as *E. coli*, *Eutropha* and *P. putida*, as well as transgenic oilseed crops, as shown by FIG. 5. Besides a polymerase that accepts the 3-hydoxybutyryl CoA and 3-hydroxyhexanoyl CoA precursors, an enzymatic activity that converts 3-hydroxyacyl ACP into 3-hydroxyacyl CoA or 3-ketoacyl ACP into 3-ketoacyl CoA is required as well. Since this activity is present in *P. putida* the corresponding gene can be identified and isolated by screening procedures. Deregulation of fatty acid biosynthesis and increased activity of this pathway subsequently provides the substrate for PHBH formation.

The critical enzymatic activity in this pathway is the conversion of the 3hydroxyacyl ACP to the CoA derivative. Thioesterases and acyl CoA synthases are widely known in their combined action can accomplish this step. Alternatively, a new activity, acyl ACP:CoA transferase, may facilitate this step in the PHA pathway and can consequently be identified in bacteria that produce PHA from oxidized carbon sources such as carbohydrates.

Growth Characteristics

For efficient PHA production, it is important that strains not lose the capability to synthesize the biopolymer for the duration of the inoculum train and the production run. Loss of any of the phb genes results in loss of product whereas loss of any of the genes that provide new monomers results in heterogeneous product formation. Both are undesirable and stable propagation of the strain is therefore required. Integration of the genes in the strains described in the examples was determined to be stable for at least 50 generations, sufficient for production in 250,000 L industrial fermentation vessels.

Growth and morphology of these recombinant PHA producers is not compromised by the presence of phb genes on the chromosome. During the selection procedures, individual integrants are selected on minimal medium plates circumventing the isolation of auxotrophic strains. Growth rates of the different phb integrants were similar to that of the wild-type *E. coli* strains from which the PHB producers were derived. The addition of the phb genes to the *E. Coli* chromosome did not affect the downstream processing of these strains, as they were still easily lysed by conventional methods.

III. Applications for the Compositions

PHAs can be used in molding applications, in particular for consumer packaging items such as bottles, cosmetic containers, diaper sheets, pens, golf tees, and personal items, such as U.S. Pat. Nos. 3,072,538; 3,107,172; and 4,900,299, which describe molded tampon applicators, and in films of pure PHA or blends or laminates of PHA with other materials such as starch esters or synthetic polymers. In many applications, the polymers are first formed into fibers and the fibers are then used to construct materials such as non-woven fabrics.

The polymers can also be used in hot-melt adhesives and pressuresensitive adhesive formulations, and to replace petrochemical polymers used in toner and developer compositions (U.S. Pat. No. 5,004,664) and as ion-conducting polymer electrolytes (U.S. Pat. No. 5,266,422). A number of features of the polyhydroxyalkanoate polymers make them particularly attractive as binders for metal powder, ceramic powder or metal/ceramic powder processing.

One of the unique features of the PHAs is that they can exist in two distinct physical forms, either as amorphous granules or as crystalline solids. PHAs therefore can be used to form a latex. PCT WO 91/13207 describes PHA latex compositions for coating paper. GB 2 292 648 A describes the use of PHA latex in architectural coating formulations. PCT WO 96/00263 describes the use of PHA latex as food coatings, in particular cheese coatings. PCT WO 92/09211 and U.S. Pat. No. 5,229,158 describe the use of PHA granule compositions for use as dairy cream substitutes. PCT WO 92/09210 and U.S. Pat. No. 5,225,227 describe the use of PHAs as flavor delivery agents in foods.

As the PHAs have become increasingly available, they have also been examined for their suitability in applications where they serve as a processing aid. One example is the use of PHA latex in the production of CRT tube components as described in PCT WO 96/17369. Key features of the usefulness of the PHAs in this application are that the coating system does not use organic solvents and that it can be readily removed during the subsequent oven treatment using less energy than conventional systems.

The PHAs can be produced in a wide variety of types depending on the hydroxyacid monomer composition (Steinbüchel & Valentin, *FEMS Microbiol Lett.* 128: 219-28 (1995)). This wide range of polymer compositions reflects an equally wide range of polymer physical properties, including a range of melting temperatures from 40 to 180° C., glass transition temperatures from −35 to 5° C., degrees of crystallinity from 0% of 80% coupled with the ability to control the rate of crystallization, and elongation to break from 5 to 500%. Poly(3hydroxybutyrate), for example, has characteristics similar to those of polypropylene, while poly(3-hydroxyoctanoate) (a copolymer of (R)-3-hydroxyoctanoate and (R)-3-hydroxyhexanoate) types behave more like elastomers, and PHAs with longer side chains behave more like waxes. The PHAs can also be plasticized and blended with other polymers or agents.

This wide range of polymer compositions reflects an equally wide range of polymer physical properties, including solubility in organic solvents, which provides a choice of a wide range of solvents. For example, copolymers of (R)3-hydroxybutyrate and other hydroxyacid comonomers have significantly different solubility characteristics from those of the PHB homopolymer. Acetone, for example, is not a good solvent for PHB, but is very useful for dissolving (R)-3-hydroxybutyrate copolymers with (R)-3-hydroxyacids containing from 6 to 12 carbon atoms (Abe, et al., *Int. J. Biol. Macromol.* 16: 115-19 (1994); Kato, et al., *Appl. Microbiol. Biotechnol.* 45: 363-70 (1996)). Similarly, Mitomo et al., *Reports on Progress in Polymer Physics in Japan*, 37: 128-29 (1994) describes the solubility of copolyesters poly(3-hydroxybutyrate-co-4-hydroxybutyrate) containing from 15 to 75 mol % 4-hydroxybutyrate residues in acetone. A number of additional solvents which are suitable for a range of PHAs have been described, for example in U.S. Pat. No. 5,213,976; U.S. Pat. No. 4,968,611; JP 95,135,985; JP 95,79,788; PCT WO 93/23554; DE 19533459; PCT WO 97/08931; and Brazil Pedido PI BR 93 02,312.

The compositions and methods of preparation and use thereof described herein are further described by the following non-limiting examples.

MATERIAL AND METHODS USED IN EXAMPLES

DNA manipulations were performed on plasmid and chromosomal DNA purified with the Qiagen plasmid preparation or Qiagen chromosomal DNA preparation kits according to manufacturers' recommendations. DNA was digested using restriction enzymes (New England Biolabs, Beverly, Mass.) according to manufacturers' recommendations. DNA fragments were isolated from 0.7% agarose-Tris/acetate/EDTA gels using a Qiagen kit. Oligonucleotides were purchased from Biosynthesis or Genesys. DNA sequences were determined by automated sequencing using a Perkin-Elmer AB1 373A sequencing machine. DNA was amplified using the polymerase-chain-reaction in 50 microliter volume using PCR-mix from Gibco-BRL (Gaithersburg, Md.) and an Ericomp DNA amplifying machine. Growth media and standard cloning procedures were as described by Sambrook et. al., (1992, in Molecular Cloning, a laboratory manual, 2nd Ed., Cold Spring Harbor Laboratory Press, Cold Spring Harbor, N.Y.).

PHA analysed by gas chromatographic (GC) analysis, carried out on the purified polymer or lyophilized cell mass. About 20 mg of sample was subjected to simultaneous extraction and butanolysis at 110° C. for 3 hours in 2 mL of a mixture containing (by volume) 90% 1-butanol and 10% concentrated hydrochloric acid, with 2 mg/mL benzoic acid added as an internal standard. The water-soluble components of the resulting mixture were removed by extraction with 3 mL water. The organic phase (1 µL at a split ratio of 1:50 at an overall flow rate of 2 mL/min.) was analyzed on an HP 5890 GC with FID detector (Hewlett-Packard Co, Palo Alto, Calif.) using an SPB-1 fused silica capillary GC column (30 m; 0.32 mm ID; 0.25 µm film; Supelco; Bellefonte, Pa.) with the following temperature profile: 80° C., 2 min; 10° C. per min. to 250° C.; 250° C., 2 min. Butylbenzoate was used as an internal standard.

Example 1

Isolation of Genes from *N. salmonicolor* Suitable for Improving the Production of PHBH Transgenic *E. coli* strains that express a chromosomally encoded PHA polymerase from *N. salmonicolor* were constructed. The PHB polymerase gene from *N. salmonicolor* was isolated and a fusion of this gene was generated with the translational sequences of the PHA polymerase gene from *Z. ramigera*, which includes the N-terminal 10 residues of the Pseudomonas enzyme. A promoterless chloramphenicol transferase gene was then placed behind the hybrid phbC gene to make aphbC-cat fusion. This fusion was randomly inserted into the *E. coli* chromosome using the pLOF or pUT system (Herrero et al.) and clones expressing the fusion were selected on chloramphenicol-containing growth medium. Expression of the fusion was consequently increased by selecting derivatives that are resistant to higher chloramphenicol levels.

PhaC was amplified from *N. salmonicolor* chromosomal DNA in the following reaction mix: 45 ml PCR Supermix (Gibco BRL, Gaithersburg, MD), 20 pmol of primers RSCP 1

```
RSCP1                                          SEQ ID NO:1
(5' GATGCCGGTCGACCCGCGGGACCGCCGCTT CTCC)
and RSPC2                                          SEQ ID NO:2
(5' TCAGCTGAAGACGTACGTACCCGGAGC),
``` in 50 ml final volume for 30 cycles: 60 seconds 95° C., 60 seconds at 55° C. and 210 seconds at 72° C., followed by a product extension step (7 minutes at 68° C.). The *N. salmonicolor* reductase gene was amplified in the following reaction: 45 ml PCR Supermix (Gibco BRL, Gaithersburg, MD), 1 mM primers

```
RD-up                                          SEQ ID NO:3
(5' CGIGTIGCICTIGTIA CIGG)
and RD-dwn                                         SEQ ID NO:4
(5' CCCATGTACAGICCICCGTT),
```

50 ml final volume for 30 cycles: 60 seconds 95° C., 60 seconds at 60° C. and 210 seconds at 72° C., followed by a product extension step (7 minutes at 68° C.). PCR products were gel purified and cloned into pCR2.1 (Invitrogen, CA). Purified fragments encoding polymerase and reductase were subsequently used in Southern blot experiments to identify a 3.6 kb phaC fragment and 4.6 kb BamHI and 4.2 kb PvuII fragments harboring phaB. Chromosomal fragments of the corresponding size were gel purified, cloned in pUC19, and clones containing the desired insert were identified by colony blot hybridization using purified phbC and phbB genes as probes.

Figure 6:
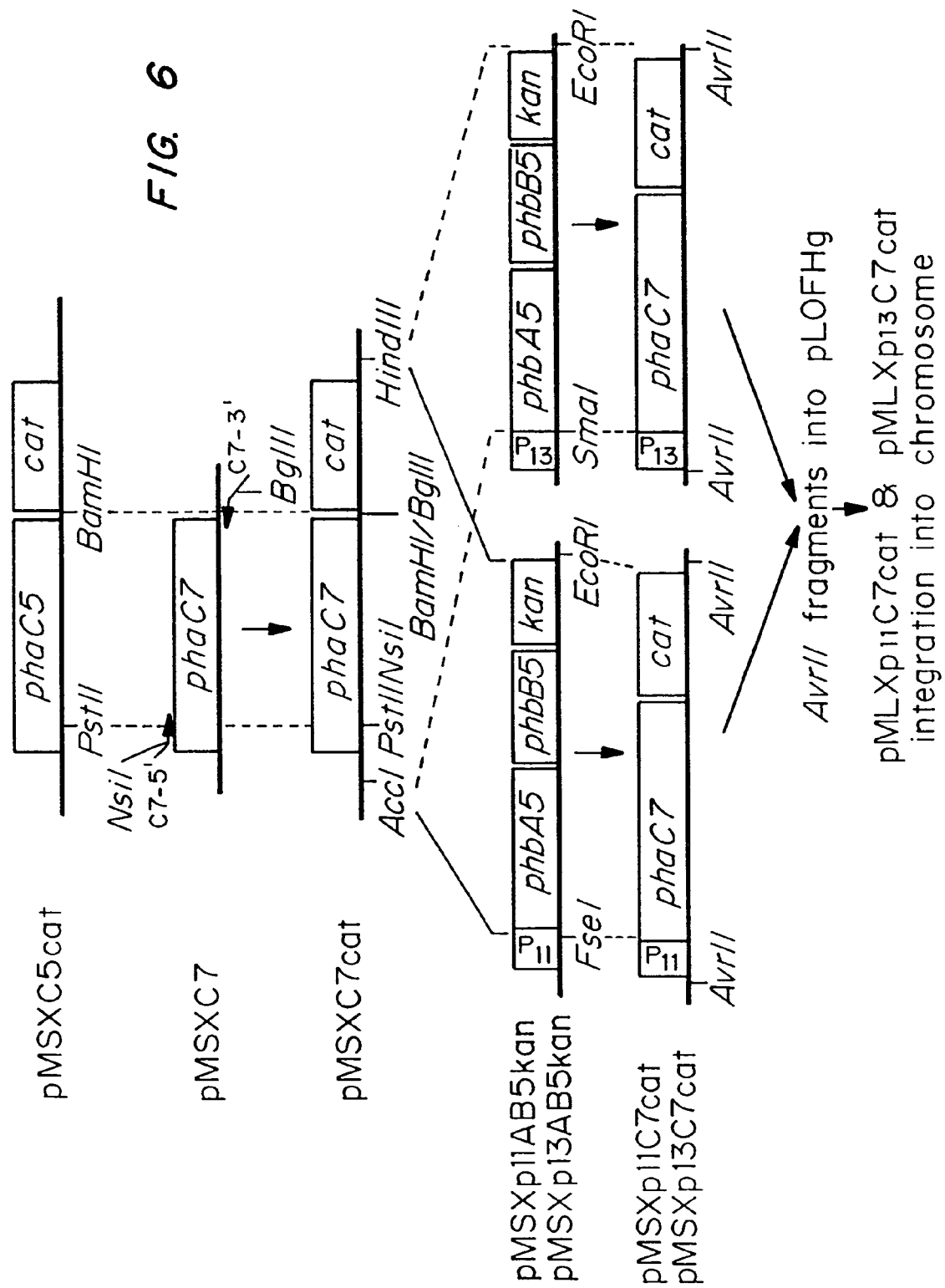
FIG. 6 is a schematic of construction of pMLXp11C7cat and pMLXp13C7cat for integration of the PHA polymerase gene from *N. salmonicolor* on the chromosome of *E. coli*.
Figure 7:
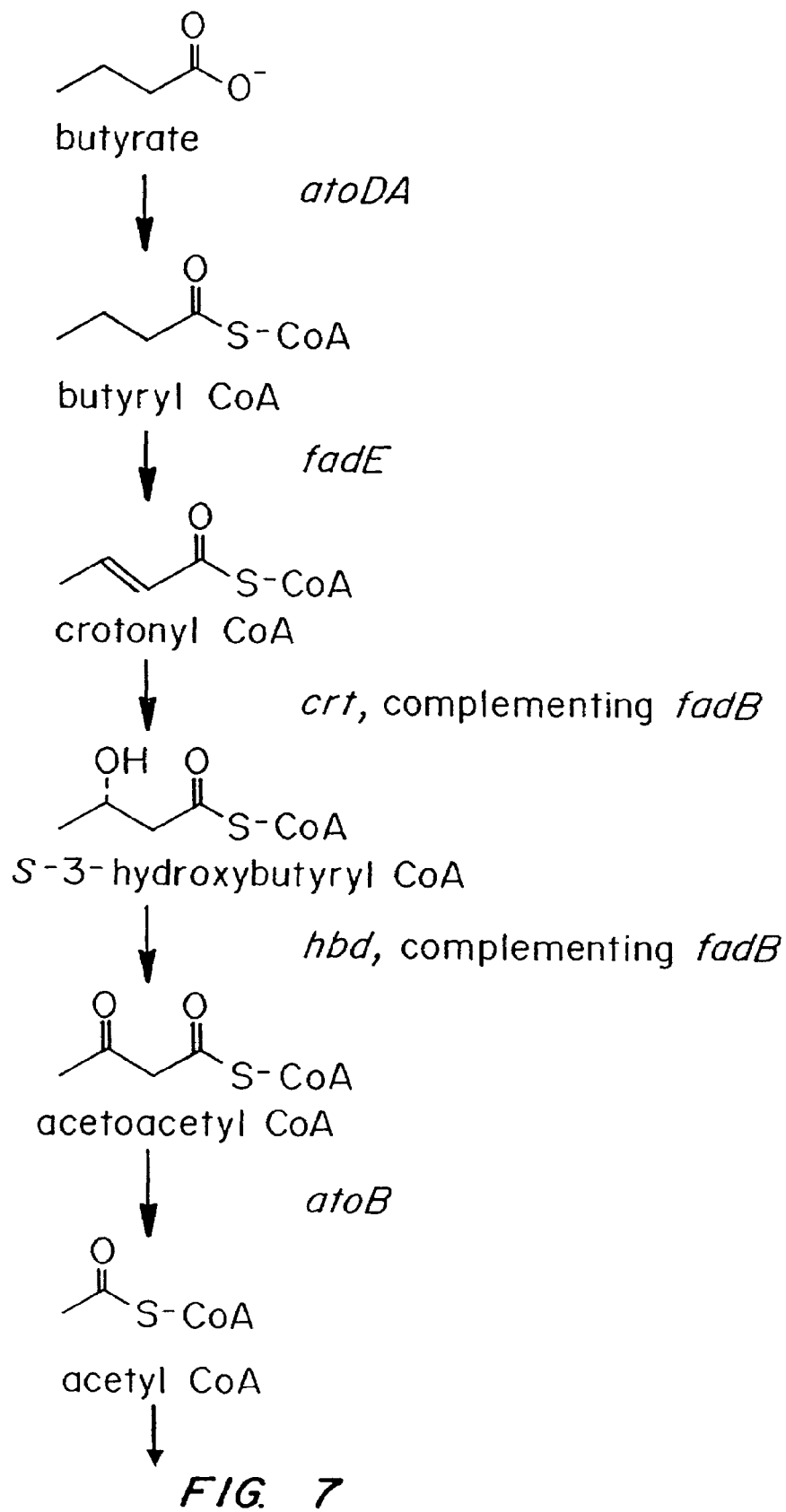
FIG. 7 is a schematic of selection for crotonase and hydroxybutyryl CoA dehydrogenase genes by complementation of an *E. coli*. fadB mutation.
Figure 8:
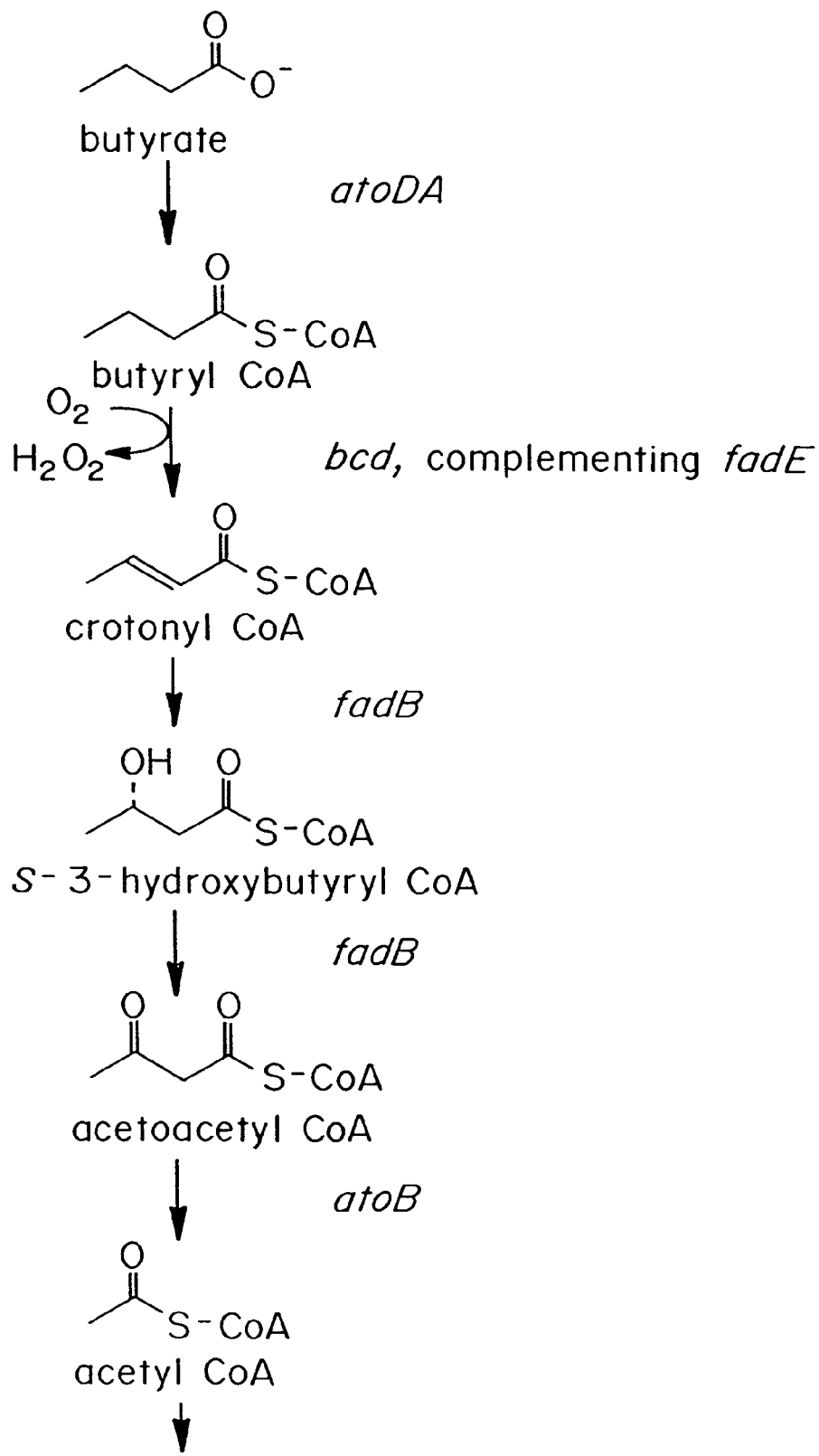
FIG. 8 is a schematic of selection for butyryl CoA dehydrogenase genes by complementation of an *E. coli* strain that is phenotypically fadE defective.
Figure 9:
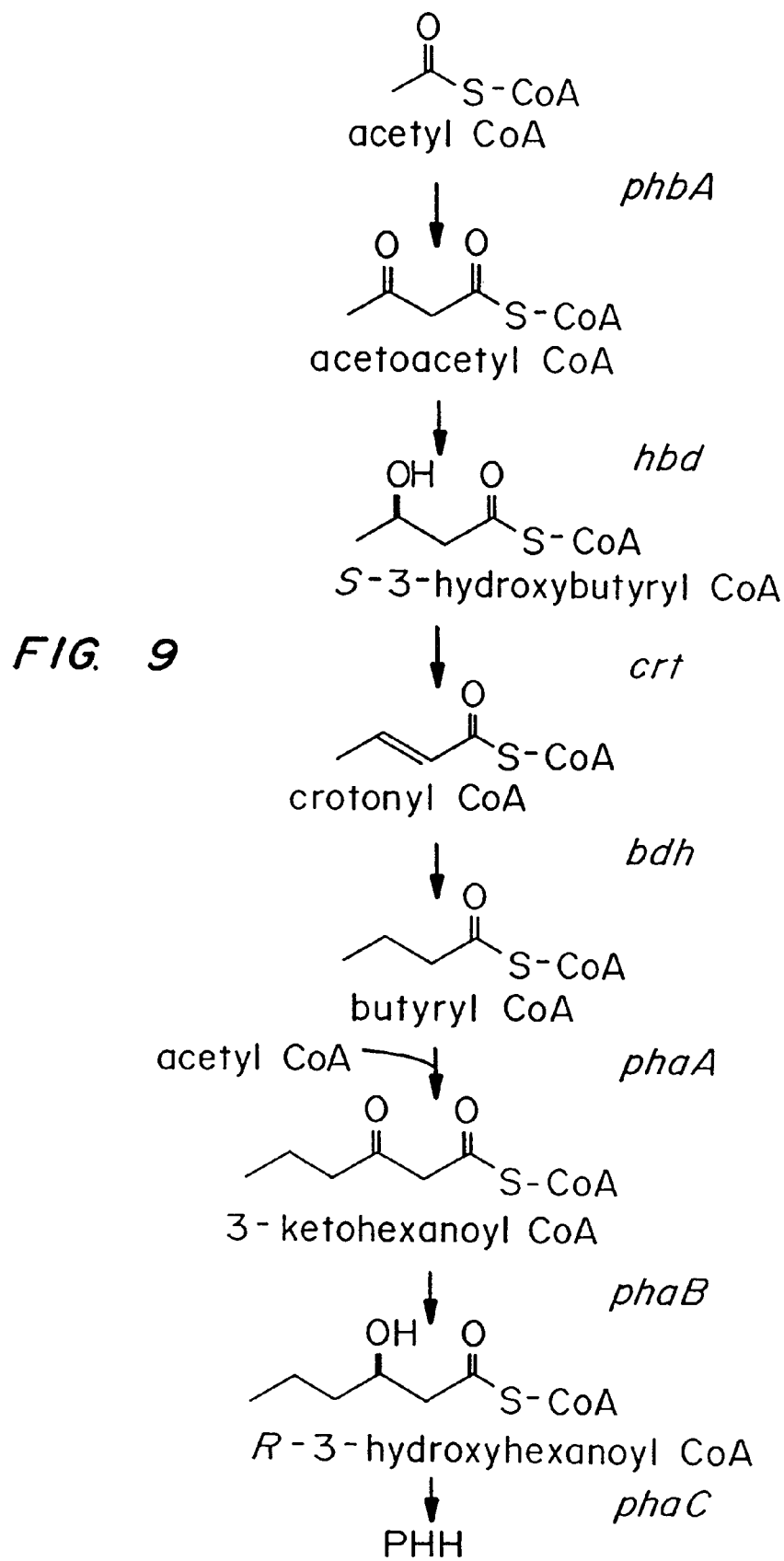
FIG. 9 is a schematic of selection for a PHBH recombinant pathway in *E. coli*. using the PHA polymerase gene phaC from *P. Putida*.

Since efficient synthesis of PHBH requires adequate expression of genes encoding enzymes involved in the biosynthetic pathway, the phaC gene from *N. salmonicolor* was reconstructed to engineer strong translational signals at the 5'end of the gene, as shown in FIG. 6. PhaC was amplified using primers

```
C7-5'                                          SEQ ID NO:5
(5' AAGTCGACCATGCATCCGATCGGCTGGGGT)
and C7-3'                                          SEQ ID NO:6
(5' ACGCTGTTCAGATCTTCGCAAGATGAATGCTAACG)
``` in a thermal cycling program entailing 30 seconds at 95° C., 30 seconds at 60° C., and 2 minutes at 72° C., followed by a 7 minute extension at 72° C.. The reaction mix contained 47 ml PCR supermix (Gibco-BRL), 0.1 nmol of each primer, and approximately 0.05 mg of pCR2.1-phaC7 as template. The PCR product was purified by phenol extraction and digested with NsiI and BglII. The restricted fragment then was cloned in the PstI and BamHI sites of pMSXC5 cat. pMSXC5cat contains a transcriptional fusion of the PHA polymerase gene from *Z. ramigera* (phaC5) and the chloroamphenicol resistance gene. The resulting plasmid contains a translational fusion resulting in a hybrid polymerase of the N-terminal 10 amino acids from PhaC5 with the *N. salmonicolor* PHA polymerase. The resulting plasmid pMSXC7cat subsequently was digested with AccI, HindIII and FspI, after which the phaC fragment was isolated for cloning behind the $p_{11}$ and $p_{13}$ promoters in FseI/EcoRI digested pMSXp$_{11}$AB5kan and SmaI/EcoRI digested pMSXp$_{13}$AB5kan. Fragments containing P$_{11}$C7cat and p$_{13}$C7cat were isolated as AvrII fragments, inserted into the SfiI site of pLOFHg, and integrated into the chromosome of *E. coli* MBX427, to yield pMLXp11C7cat and pMLXp13C7cat.

Alternative 3-hydroxyhexanoyl CoA accepting PHA polymerase genes can be obtained from organisms that have been shown to incorporate this monomer, including *A. caviae, C. testosteroni, T. pfenigii*, and possibly *P. denitrificans* and *S. natans*. These genes can be expressed in *E. coli* according to the same procedures described above.

Example 2

PHBH Synthesis in *E. coli* from Butyrate

Endogenous synthesis of R-3-hydroxyhexanoyl CoA can proceed after condensation of butyryl CoA with acetyl CoA followed by a reductive step. This pathway requires only a broad substrate range reductase and a polymerase that accepts 3-hydroxyhexanoyl CoA. Butyrate is taken up by *E. coli* and converted to butyryl CoA by the atoDA gene products. Degradation of butyryl CoA is dependent on atoB and the fad regulon which is not induced by butyrate.

Plasmid pMBXc12J12 was constructed by inserting the 2.4 Kb ApoI fragment containing the *A. caviae* phaC gene encoding a PHA synthase (Fukui & Dci, *J Bacteriol.* 179: 4821-30 (1997)) into the EcoRI site of pUC18. Plasmid pSU 18-AB1 contains the *R. eutropha* phbAB genes under the control of an IPTG-inducible promoter in the vector pSU18 (Martinez et. al., Gene 66: 1659-20 (1988)). PHBH was produced from glucose and butyrate in *E. coli* MBX1325 (identical to strain DC679, mel, fadR, atoC (con) adhC81 (Clark & Rod, *J. MOL. Biol. Evol.* 25: 151 (1987)) containing plasmids pMBXC12J12and pSU18-AB1as follows. The transformed cells (1L) were grown in LB containing 20 mM butyrate for 24 hours at 30° C. and harvested by centrifugation. The PHA polymer was purified from lyophilized cells by extraction with chloroform for 16 hours and the PHA precipitated in a 5- to 10-fold excess of methanol. The precipitated polymer was analyzed by gas chromatography and identified as PHBH copolymer containing 1.0 %HH comonomer.

Example 3

PHBH Synthesis in *E. coli* Using the Butyrate Fermentation Pathway

The butyrate fermentation pathway is shown in FIG. 3. Enzymes required for 3-hydroxyhexanoate synthesis are encoded byphbA$_x$, hbd, crt, bdh, phbA$_y$, phbB and phbC, in which x and y indicate identical or different thiolases. The sources for these genes are *Z. ramigera* (phbA$_{xy}$), *C. acetobutylicum* (hbd, cr, bdh) and *N. salmonicolor* (phbB and phbC).

Crt and hbd were isolated by polymerase chain reaction using pC10 (Boynton et al) as template using the following primers:

```
5' crt:                                  SEQ ID NO:7
5' GGGGATCCGAATTCAGGAGGTTTTTATGGAACTAAACAA
TGTCATCC;

3' crt:                                  SEQ ID NO:8
5' GGAATTCGAGCTCCTATCTATTTTTGAAGCC;

5' hbd:                                  SEQ ID NO:9
5' GGAATTCGGTACCAGGAGGTTTTTATGAAAAAGGTATGT
GTTATAGG;

3' hbd:                                  SEQ ID NO:10
5' GGAATTCCCCGGGTTATTTTGAATAATCGTAGAAACC.
```

PCR products were purified, digested with EcoRI/SacI (crt) or KpnI/SmaI (hbd), and subsequently cloned in the corresponding sites of pUC18-Sfi, resulting in pMSXcrt-hbd.

Bdh was isolated by polymerase chain reaction using pC10 (Boynton et al.) as template and the following primers:

```
5' bcd:                                  SEQ ID NO:11
GGAATTCCTGCAGAGGAGGTTTTATGGATTTTAATTTAACAAG
AG;

3' bcd:                                  SEQ ID NO:12
GGAATTCGCATGCT TATCTAAAAATTTTTCCTG.
```

The PCR product was purified, digested with PstI/SphI, and subsequently cloned in the corresponding sites of pMSXcrt-hbd, resulting in pMSXcrt-hbd-bcd.

The original operon from pC10 contained etfAB encoding for a putative electron transfer chain. The crt-hbd-bcd operon may not be active in the absence of this operon so the etfA and etfB genes were amplified from the pC10(Boynton et al.) with the primers

```
5' etfBA:                                SEQ ID NO:13
5' GGAATTCGGATCCAGGAGGTTTTATGAATATAGTTGT
TTGTTTAAACA AGTTCC
and 3' etfBA:                                SEQ ID NO:14
5' GGAATTCGTCGACTTAATTATTAGCAGCTTTAACT TGAGC.
```

The PCR product was purified, digested with BamHI and SalI, and subsequently cloned in the corresponding sites of pUC18-SfiI, resulting in pMSXetfAB. The etfAB genes can be easily cloned into the pMSXcrt-hbd-bcd plasmid in the BamHI/SalI sites.

Example 4

PHBH Synthesis in *E. coli* Using a Fatty Acid Oxidation Pathway

The fatty acid oxidation pathway is shown in FIG. 4. R-3 hydroxyhexanoyl CoA can be obtained from fatty acid oxidation intermediates by epimerization of S-3-hydroxyhexanoyl-CoA, reduction of 3-ketohexanoyl-CoA or by hydration of the enoyl-CoA by D-specific hydratase. The *E. coli* strain MBX240 is a derivative of the strain XL1-Blue (Stratagebe, San Diego, CA) constructed by inserting a copy of the *R. eutropha* phbC gene into the chromosome. This strain does not produce PHAs from sugars or fatty acids because of the absence of enzymes for converting acetyl-CoA or fatty acid oxidation intermediates into the R-3-hydroxyacyl-CoA monomers. The phaJ gene encoding an enoyl-CoA hydratase (Fukui and Doi, *J. Bacteriol.* 179: 4821-30 (1997)), was isolated from chromosomal DNA prepared from *A. caviae* strain FA-440 (obtained from the Japanese Culture Collection under accession number FERM BP 3432 (U.S. Pat. No. 5,292,860) by the polymerase chain reaction using the primers:

Ac3-5': SEQ ID NO:15
AGAATTCAGGAGGACGCCGCATGAGCGCACAATCCCTGG
and

Ac3-3': SEQ ID NO:16
TTCCTGCAGCTCAAGGCAGCTTGACCACG and a PCR reaction mixture obtained from Life Technologies (Gaithersburg, MD). The PCR program was 30 cycles of (95° C., 45s; 55° C., 45s; 72° C., 1 min.). Following PCR, the DNA fragment was digested to completion with EcoRI and PstI, gel purified and ligated into the EcoRI/PstI sites of plasmid pUC18Sfi (Herrero et. al.), to obtain plasmid pMTXJ12. Transformants of E. coli MBX 240 containing plasmid pMTXJ12 were grown in Luria-Bertani medium containing 10mM octanoate and 1mM oleate and ampicillin at 100 µg/ml. After growth at 37° C. for 48 hours, 50 ml of cells were harvested by centrifugation and lyophilized. Lyophilized cells were extracted with 8 ml chloroform for 16 hours and the PHA precipitated in a 10-fold excess of ethanol at 4° C. The precipitated polymer was analyzed by gas chromatography and identified as PHBH copolymer containing 2.6% HH comonomer.

Example 5

Production of PHBH copolymers From Butanol in E.coli Expressing the A. caviae PHA synthase and the R. eutropha Thiolase and Reductase Genes PHBH was produced from glucose and butyrate in E. coli MBX1326 (identical to strain DC698, mel, fadR atoC (con) adhC81, adhR30aceX, Clark & Rod, J. Mol. Biol. Evol. 25: 151(1987)) containing plasmids pMBXC12J12 and pSU18-AB1 as follows. The transformed cells were grown in 1L LB medium containing 5g/L butanol. Cells were harvested and analyzed as for Example 1. The genetically engineered cells produced a PHBH copolymer containing 1.2% HH.

Example 6

PHBH Synthesis in E. coli Using a Fatty Acid Biosynthesis Pathway

The fatty acid biosynthesis pathway is shown in FIG. 5. R-3hydroxyhexanoyl CoA also can be provided from intermediates from fatty acid biosynthesis. In P. putida, 3-hydroxyacyl CoA are provided from this pathway when this bacterium is grown on glucose or other carbohydrates. This pathway requires an activity that converts acyl ACP into acyl CoA, a reaction catalyzed by an ACP/CoA transacylase or by the combined action of an acyl ACP thioesterase and acyl CoA synthase. Introduction of this pathway in an E. coli strain that expresses the PHB biosynthetic genes and that has a constitutive fatty acid biosynthetic regulon (fadR$^+$), such as MBX689, results in the synthesis of R-3-hydroxyhexanoyl CoA.

Figure 10:
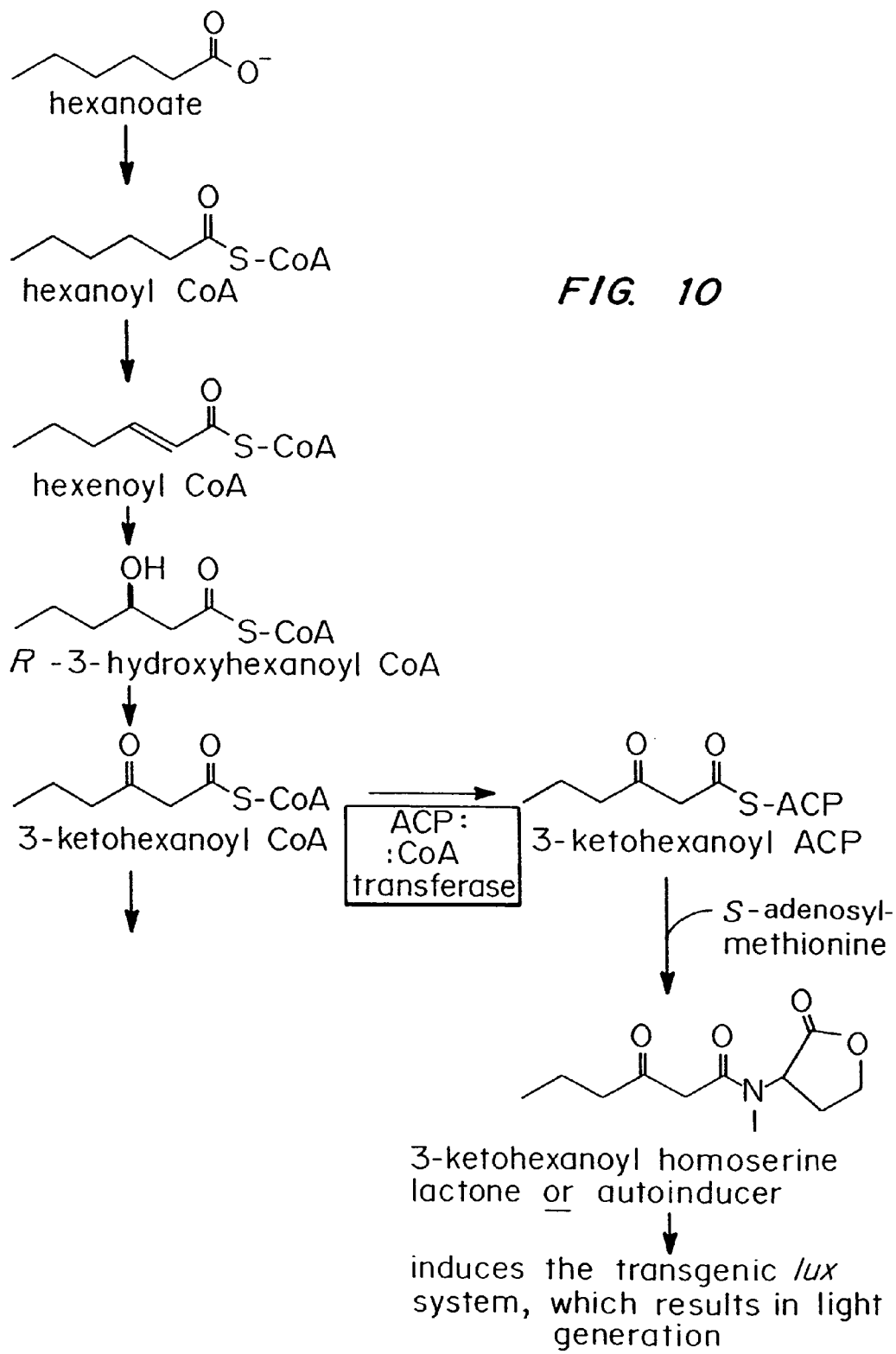
FIG. 10 is a schematic of a preferred screening procedure for genes encoding enzymes that convert acyl ACP to acyl CoA with the use of the *Vibrio fischeri* lux system.

Genes encoding the enzymes that facilitate the ACP to CoA transacylation are isolated in the following screen which employs the lux system from V. fischeri, as shown in FIG. 10. Induction of the lux genes depends on the synthesis of autoinducer 3-ketohexanoyl homoserine lactone. The precursors for this molecule are S-adenosylmethionine and 3-ketohexanoyl ACP. E. coli CGSC5638 has a mutation in the fabD gene encoding malonyl transacylase (Bouquin et al., Mol. Gen. Genet. 246: 628 (1995)) and is unable to synthesize acetoacetyl ACP. Hexanoate is provided to these cells for synthesis of long side chain fatty acids. In addition, a fadR mutation is introduced to degrade hexanoate to 3-ketohexanoyl CoA. In order for the cells to induce expression of the lux system, 3-kektohexanoyl CoA must be converted to 3-ketohexanoyl ACP. Gene libraries of various organisms then can be screened in this host, selecting positive clones for their ability to induce lux expression, which is identified as light emission due to the formation of inducer 3-ketohexanoyl homoserine lactone. Gene libraries are readily constructed from organisms of choice by isolating genomic DNA and cloning a representative collection of DNA fragments in plasmid vectors. Representative libraries should have 5,000 to 100,000 individual colonies. Libraries are made either as a broad-host-range library in vectors such as pLAFR3 or as E coli libraries in vectors such as pUC19 or pBR322. Depending on the type of library and the method of introducing the library in the host of choice, the genomic DNA fragments are either large (17-30 kb) or relatively small (2-6 kb). Libraries are introduced into the screening strains by electroporation, transformation, or conjugation, depending on the host and the vector used.

Modifications and variations of the present invention will be obvious to those of skill in the art from the foregoing detailed description. Such modifications and variations are intended to come within the scope of the following claims.

We claim:

1. A method for the biological production of polyhydroxyalkanoates containing 3-hydroxyhexanoate in plants, comprising synthesizing the polyhydroxyalkanoate in plants expressing an enzyme selected from the group consisting of PHB polymerase, PHA polymerase, and β-ketoacyl-CoA reductase, wherein the plants are genetically engineered by integration into the chromosome of one or more genes encoding one or more enzymes forming a fatty acid oxidation complex, wherein the fatty acid oxidation complex comprises enzymes selected from the group consisting of enzymes epimerizing S-3 hydroxyhexanoyl CoA and enzymes reducing 3-ketohexanoyl CoA.

2. The method of claim 1 wherein the plant is selected from the group consisting of oil crop plants and starch accumulating plants.

3. The method of claim 2 wherein the plant is selected from the group consisting of Brassica, sunflower, soybean, corn, safflower, flax, palm, coconut, potato, tapioca, cassava, alfalfa, grass, and tobacco.

4. The method of claim 1 wherein the plant is genetically engineered to express or overexpress a PHA polymerase incorporating C6 substrates.

5. The method of claim 4 wherein the enzyme is derived from *Aeromonas caviae, Comamonas testosteroni, Thiocapsia pfenigii, Chromatium vinosum, Bacillus cereus, Nocardia carolina, Nocardia salmonicolor, Rhodococcus ruber, Rhodococcus rhodocrous*, and *Rhodospirilum rubrum*.

6. The method of claim 1 wherein the plant is genetically engineered to redirect metabolites to production of 3-hydroxyhexanoyl-CoA.

7. The method of claim 6 wherein the plant is genetically engineered using a D-specific enoyl-CoA hydratase gene.

8. The method of claim 7 wherein the hydratase gene is isolated from a bacteria selected from the group consisting of *R. eutropha, Klebsiella aerogenes, P. putida*, and *Aeromonas caviae*.

9. The method of claim 6 wherein the plant is genetically engineered using a butyrate fermentation pathway.

10. The method of claim 9 wherein the butyrate fermentation pathway is from *Clostridium acetobutylicium* or *Thermoanaerobacterium thermosaccharolyticum*.

11. The method of claim 9 wherein the plant is genetically engineered to convert butyrate to butyryl CoA or butyryl CoA to crotonyl CoA.

12. The method of claim 9 wherein the plant is genetically engineered to express a broad range reductase that is active on C6 substrates.

13. The method of claim 9 wherein the plant is genetically engineered to express a polymerase that accepts 3-hydroxyhexanoyl CoA.

14. The method of claim 9 wherein the plant is genetically engineered to express a thiolase accepting acetoacetyl CoA.

15. The method of claim 9 wherein the plant is genetically engineered to express an enzyme selected from the group consisting of thiolases specific for 3-ketohexanoyl CoA, reductase active on 3-ketohexanoyl CoA, PHA polymerase that accepts 3-hydroxybutyryl CoA and 3-hydroxyhexanoyl CoA.

16. The method of claim 6 wherein the plant is genetically engineered to integrate one or more nucleic acids encoding fatty acid biosynthetic enzymes derived from *E. coli*.

17. The method of claim 16 wherein the fatty acid biosynthetic enzymes are enzymes converting acyl ACP to acyl CoA.

18. The method of claim 17 where the enzymes are selected from the group consisting of ACP-CoA transacylase, acyl ACP thioesterase, and acyl CoA synthase.

19. The method of claim 18 wherein the enzymes are acyl ACP thioesterase and acyl CoA synthase.

20. The method of claim 1 wherein the fatty acid oxidation complex comprises enzymes epimerizing S-3 hydroxyhexanoyl CoA and enzymes reducing 3-ketohexanoyl CoA.

21. The method of claim 20 wherein the enzymes are derived from *Nocardia salmonicolor*.

22. The method of claim 20 wherein the enzymes for epimerization are derived from *Pseudomonas putida* FaoAB complex.

* * * * *